(12) United States Patent
Higuchi et al.

(10) Patent No.: US 10,006,831 B2
(45) Date of Patent: *Jun. 26, 2018

(54) END FACE OBSERVATION DEVICE

(71) Applicant: NIPPON TELEGRAPH AND TELEPHONE CORPORATION, Tokyo (JP)

(72) Inventors: Yuichi Higuchi, Tokyo (JP); Koichi Hadama, Tokyo (JP); Joji Yamaguchi, Tokyo (JP); Toru Miura, Tokyo (JP); Etsu Hashimoto, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/104,717

(22) PCT Filed: Dec. 16, 2014

(86) PCT No.: PCT/JP2014/083244
§ 371 (c)(1),
(2) Date: Jun. 15, 2016

(87) PCT Pub. No.: WO2015/093470
PCT Pub. Date: Jun. 25, 2015

(65) Prior Publication Data
US 2016/0313211 A1    Oct. 27, 2016

(30) Foreign Application Priority Data

Dec. 16, 2013 (JP) .................................. 2013-259642
Mar. 10, 2014 (JP) .................................. 2014-045943

(51) Int. Cl.
*G01M 11/00* (2006.01)
*G02B 27/00* (2006.01)
(Continued)

(52) U.S. Cl.
CPC .......... *G01M 11/31* (2013.01); *G01M 11/088* (2013.01); *G02B 6/385* (2013.01);
(Continued)

(58) Field of Classification Search
CPC .. G02B 27/0006; G02B 6/385; G02B 6/3866; G01M 11/088; G01M 11/31;
(Continued)

(56) References Cited

U.S. PATENT DOCUMENTS 3,027,477 A * 3/1962 Sheldon ............ A61B 1/00165
313/110
3,205,390 A * 9/1965 Sheldon ............ A61B 1/00165
250/227.2
(Continued)

FOREIGN PATENT DOCUMENTS

JP    H02-069606 A    3/1990
JP    05-079814 A     3/1993
(Continued)

OTHER PUBLICATIONS

Machine translation of JP 2015-169866 A published on Sep. 28, 2015 (Application JP 2014-045945 filed on Mar. 10, 2014); 66 pages.*

*Primary Examiner* — Gordon J Stock, Jr.
(74) *Attorney, Agent, or Firm* — Womble Bond Dickinson (US) LLP

(57) ABSTRACT

An end face observation device (101) of this invention includes a first lens (12) including a missing portion (1200) extending through in an optical axis direction, a light source (14) configured to generate light that irradiates an end face (200A) of an observation target via the first lens, and an image capturing element (15) configured to receive an image of the end face of the observation target via the first lens. This can implement an end face observation device that (Continued)

integrates a structure configured to operate the end face of the observation target with an observation device configured to observe the end face by inserting the structure configured to operate the end face of the observation target into the missing portion of the first lens.

24 Claims, 13 Drawing Sheets

(51) Int. Cl.
  *G02B 6/38* (2006.01)
  *G01M 11/08* (2006.01)
  *G01N 21/88* (2006.01)
(52) U.S. Cl.
  CPC ....... *G02B 6/3866* (2013.01); *G02B 27/0006* (2013.01); *G01N 21/88* (2013.01)
(58) Field of Classification Search
  CPC .............. G01N 21/88; G01N 21/8803; G01N 21/8806; G01N 21/94; G01N 21/95; G01N 21/9515; G01N 21/952; G01N 21/958; G01N 2021/8822; G01N 2021/8825; G01N 2021/9511
  See application file for complete search history.

(56) References Cited

U.S. PATENT DOCUMENTS

| | | | | |
|---|---|---|---|---|
| 3,676,671 A * | 7/1972 | Sheldon | ................ | H01J 31/28 250/227.2 |
| 4,412,720 A * | 11/1983 | Costa | .................... | G01M 11/31 385/11 |
| 5,179,419 A * | 1/1993 | Palmquist | ........... | G01N 21/952 356/237.2 |
| 5,724,127 A * | 3/1998 | Csipkes | ................ | G01M 11/31 356/73.1 |
| 6,411,838 B1 * | 6/2002 | Nordstrom | ........... | A61B 5/0059 600/407 |
| 6,454,437 B1 * | 9/2002 | Kelly | ........................ | G01J 3/10 359/287 |
| 8,988,670 B2 * | 3/2015 | Zhou | ........................ | B08B 5/02 356/73.1 |
| 9,528,908 B2 * | 12/2016 | Wilson | ................... | G01M 11/31 |
| 9,599,507 B2 * | 3/2017 | Pawluczyk | ........... | G01J 3/0243 |
| 2004/0141175 A1 * | 7/2004 | Baldwin | ............ | G01N 21/8806 356/237.2 |
| 2008/0073485 A1 * | 3/2008 | Jahn | ................... | G01M 11/3154 250/201.2 |
| 2010/0295938 A1 * | 11/2010 | Hahn | ................. | G01N 21/9501 348/126 |
| 2013/0229650 A1 * | 9/2013 | Wilson | ...................... | B08B 1/00 356/73.1 |
| 2013/0321906 A1 * | 12/2013 | Kriofske | ................ | G02B 27/00 359/363 |
| 2015/0157194 A1 * | 6/2015 | Okuda | ............... | G02B 23/2446 600/109 |
| 2015/0253516 A1 * | 9/2015 | Miura | .................... | G01M 11/31 348/143 |

FOREIGN PATENT DOCUMENTS

| | | |
|---|---|---|
| JP | H08-101128 A | 4/1996 |
| JP | H08-105818 A | 4/1996 |
| JP | H10-002714 A | 1/1998 |
| JP | H10-019728 A | 1/1998 |
| JP | 2003-050206 A | 2/2003 |
| JP | 2004-219602 A | 8/2004 |
| JP | 2012-093636 A | 5/2012 |
| JP | 2012-103204 A | 5/2012 |
| JP | 2015-010850 A | 1/2015 |
| JP | 2015-010851 A | 1/2015 |

* cited by examiner

FIG. 1
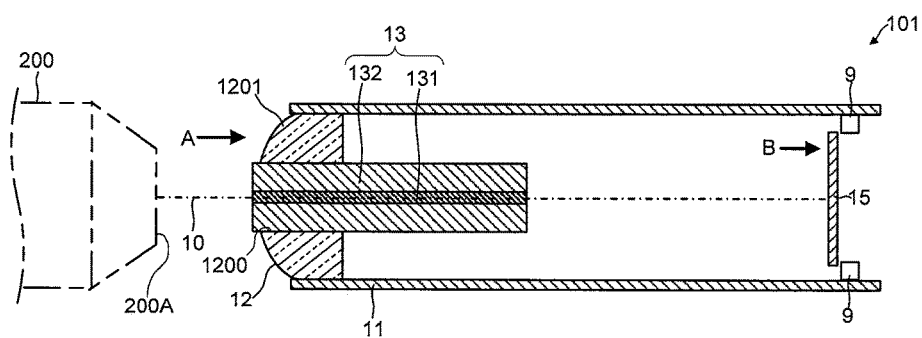
FIG. 2A     FIG. 2B     FIG. 2C
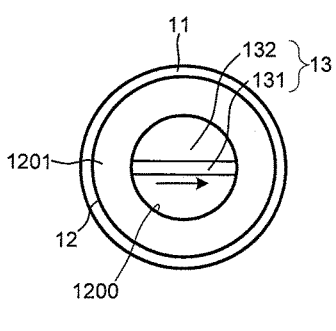 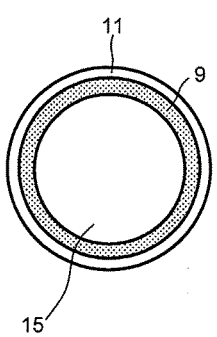 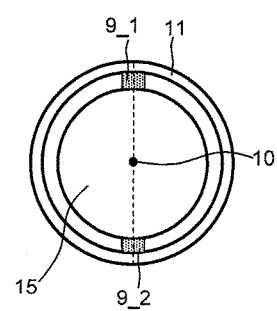

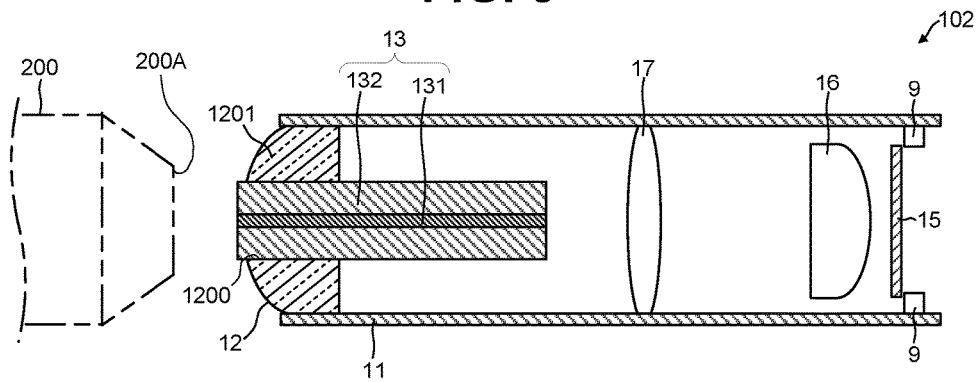
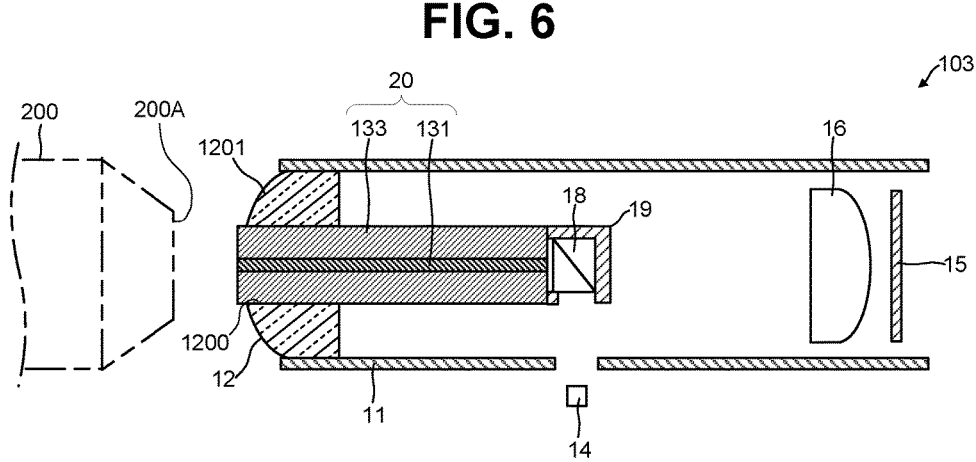
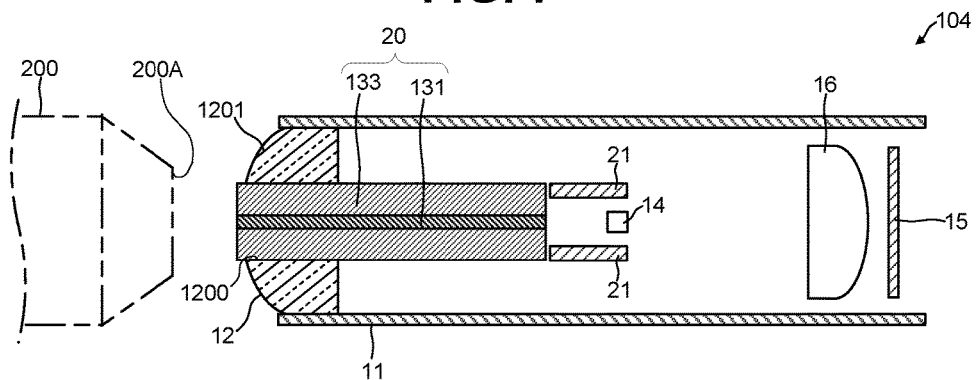

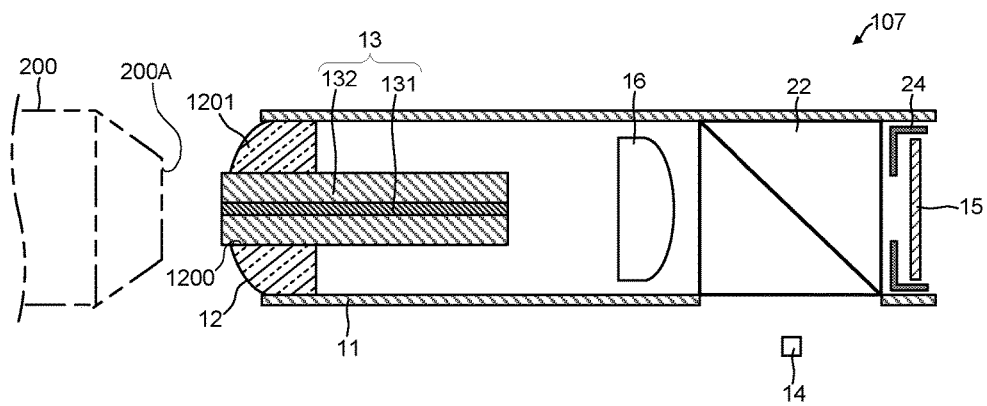
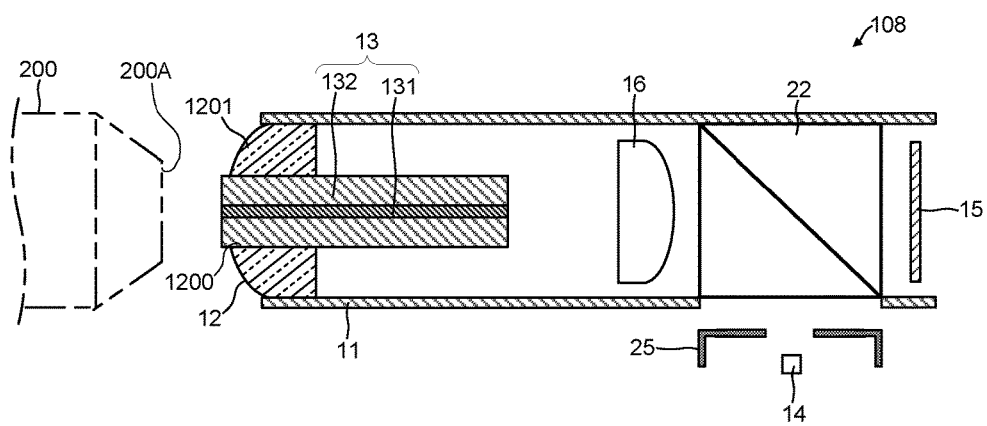
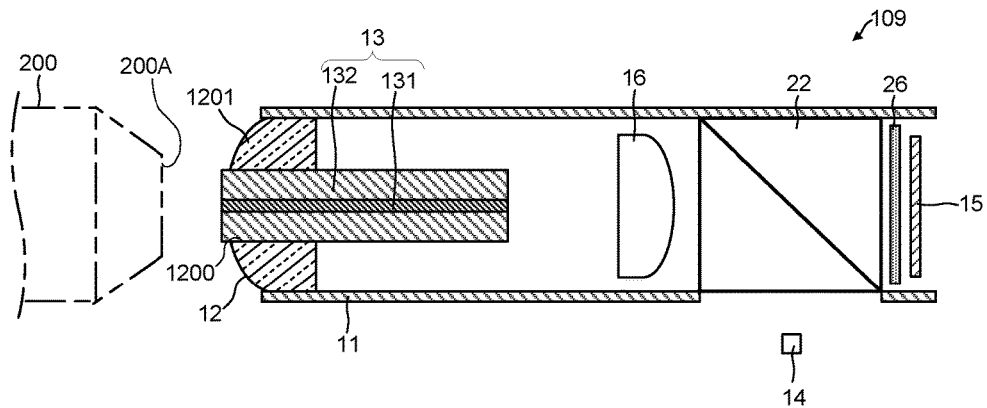

END FACE OBSERVATION DEVICE

TECHNICAL FIELD

The present invention relates to an end face observation device that observes the end face state of an optical connector.

BACKGROUND ART

In optical communication, an optical connector is an indispensable component used to connect various kinds of network devices and optical fibers. Reducing a loss in the optical connector is very important to implement satisfactory optical communication. Main factors of losses in the optical connector are dust or foreign substance adhesion and dirt on the connector end face. For this reason, when connecting the optical connector, cleaning and observation of the connector end face are important operations.

More specifically, the optical connector is formed from a plug that is a male connector and a receptacle that is a female connector and serves as an opening to receive a plug in a network device or the like. There have conventionally been proposed cleaners and end face observation devices used to clean and observe the plug and the receptacle.

For example, patent literature 1 discloses a cleaner including a cleaner tape for a connector end face in a receptacle. In addition, patent literature 2 discloses an observation device for a connector end face in a receptacle. When connecting a connector, a cleaning operation and an observation operation for the optical connector are performed using such devices.

RELATED ART LITERATURE

Patent Literature

Patent Literature 1: Japanese Patent Laid-Open No. 2004-219602
Patent Literature 2: Japanese Patent Laid-Open No. 10-19728

DISCLOSURE OF INVENTION

Problem to be Solved by the Invention

However, the conventional cleaning device and observation device as described above are provided as separate devices in general. The devices are separately prepared, and the cleaning operation and the observation operation are performed by exchanging the devices as needed. For this reason, the operations are inevitably cumbersome.

It is an object of the present invention to provide an end face observation device easy to operate and capable of shortening the operation time.

Means of Solution to the Problem

An end face observation device according to the present invention comprises a first lens including a missing portion extending through in an optical axis direction, a light source configured to generate light that irradiates an end face of an observation target via the first lens, and an image capturing element configured to receive an image of the end face of the observation target via the first lens.

Effect of the Invention

According to the present invention, it is possible to implement an end face observation device that integrates a structure configured to operate an end face of an observation target with an observation device configured to observe the end face by inserting the structure configured to operate the end face of the observation target into a missing portion of a first lens. This makes it possible to provide an end face observation device easy to operate and capable of shortening the operation time.

BRIEF DESCRIPTION OF DRAWINGS

FIG. 1 is a view showing the arrangement of an end face observation device according to the first embodiment;

FIG. 2A is a view showing a detailed example of the arrangement of a cleaning mechanism in the end face observation device according to the first embodiment;

FIG. 2B is a view showing an example of the arrangement of a light source in the end face observation device according to the first embodiment;

FIG. 2C is a view showing another example of the arrangement of the light source in the end face observation device according to the first embodiment;

FIG. 5 is a view showing another arrangement of the end face observation device according to the second embodiment;

FIG. 6 is a view showing the arrangement of an end face observation device according to the third embodiment;

FIG. 7 is a view showing the arrangement of an end face observation device according to the fourth embodiment;

FIG. 10 is a view showing the arrangement of an end face observation device according to the seventh embodiment;

FIG. 11 is a view showing the arrangement of an end face observation device according to the eighth embodiment;

FIG. 12 is a view showing the arrangement of an end face observation device according to the ninth embodiment;

BEST MODE FOR CARRYING OUT THE INVENTION

Figure 3A:
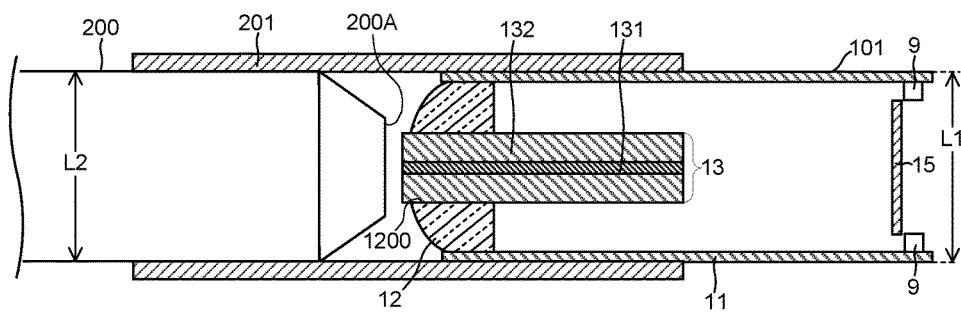
FIG. 3A is a view for explaining a method of using the end face observation device according to the first embodiment.

1. Outline of End Face Observation Device According to Present Invention

The outline of an end face observation device according to the present invention will be described.

(1) (Main Body of End Face Observation Device)

An end face observation device (100-124) according to the present invention comprises a first lens (12) including a missing portion extending through in an optical axis direction, a light source (9, 14) configured to generate light that irradiates an end face (200A) of an observation target (200) via the first lens, and an image capturing element (15) configured to receive an image of the end face of the observation target via the first lens.

(2) (End Face Observation Device With Structure Being Inserted into Missing Portion of Lens)

The end face observation device (101) described in (1) may further comprise a structure (13) inserted into the missing portion of the first lens and configured to operate the end face of the observation target.

(3) (Cleaning Mechanism)

In the end face observation device according to (2), the structure may include a cleaning mechanism configured to clean the end face of the observation target.

(4) (First Lens is Coaxial to Optical Axis)

In the end face observation device (101, 102) according to any one of (1) to (3), the light source and the first lens are arranged coaxially.

(5) (Ring-Shaped Lens)

In the end face observation device according to any one of (1) to (4), the first lens may have a ring shape.

(6) (Ring-Shaped Light Source)

In the end face observation device (101, 102) according to any one of (1) to (5), the light source may have a ring shape.

(7) (Reflected Light and Illumination Light Commonly Propagate in Same Medium)

The end face observation device (101, 102) according to any one of (1) to (6) may further comprise a tubular case, the first lens and the structure may be arranged at one end of the tubular case, the light source and the image capturing element may be arranged at the other end of the tubular case, and illumination light from the light source and reflected light from the end face of the observation target may propagate through a common space in the case.

(8) (Second Lens)

The end face observation device (102) according to any one of (1) to (7) may further comprise a second lens (16) provided on an optical axis between the first lens and the image capturing element.

(9) (Transparent Member)

The end face observation device according to (8) may further comprise a transparent member (17) provided on the optical axis between the first lens and the second lens.

(10) (Optical Element)

The end face observation device (105-124) according to any one of (1) to (3) may further comprise an optical element (22, 30, 34, 35) provided on an optical axis between the first lens and the image capturing element and configured to partially reflect incident light and partially passes the incident light.

(11) (Optical Element: Beam Splitter or Half Mirror)

In the end face observation device according to (10), the optical element may comprise one of a beam splitter and a half mirror.

(12) (Optical Element: Nonparallel Half Mirror)

In the end face observation device (121) according to (10), the optical element may comprise a half mirror (34) whose reflecting surface and transmitting surface are nonparallel.

(13) (Optical Element: Beam Splitter in Which Relative Angle is Not 45°)

In the end face observation device (122) according to (10), the optical element may comprise a beam splitter (35), z which has a transmitting surface facing said light source and a reflecting surface that partially reflects light that enters via the transmitting surface, wherein a relative angle between the transmitting surface and the reflecting surface is not 45°.

(14) (Second Lens on Image Capturing Element Side)

The end face observation device (105) according to any one of (10) to (13) may further comprise a second lens (16) provided on an optical axis between the optical element and the image capturing element.

(15) (Second Lens on First Lens Side)

The end face observation device (106-124) according to any one of (10) to (13) may further comprise a second lens (16, 31) provided on an optical axis between the first lens and the optical element.

(16) (Third Lens on First Lens Side)

The end face observation device (106, 123, 124) according to (15) may further comprise a third lens (17, 32) provided on the optical axis between the first lens and the second lens.

(17) (Fourth Lens on Light Source Side)

The end face observation device (106) according to (15) may further comprise a fourth lens (23) provided on an optical axis between the light source and the optical element.

(18) (Second Lens+Optical Component on Image Capturing Element Side)

The end face observation device (107, 109, 111, 114-122) according to any one of (10) to (17) may further comprise at least one of an iris (24), a wavelength filter (26), and a polarization filter (28) on an optical axis between the image capturing element and the optical element.

(19) (Second Lens+Optical Component on Light Source Side)

The end face observation device (108, 110, 112, 115-122) according to any one of (10) to (18) may further comprise at least one of an iris (25), a wavelength filter (27), and a polarization filter (29) on an optical axis between the light source and the optical element.

(20) (Transparent Member)

The end face observation device (106A, 106E) according to any one of (10) to (19) may further comprise a transparent material (17) provided on the optical axis between the first lens and the optical element.

(21) (Operation Portion of Structure)

The end face observation device (124) according to any one of (10) to (19) may further comprise an operation portion (36) provided on the optical axis between the first lens and the optical element and made of a transparent material, and the operation portion may be connected to the structure and may be movable in the optical axis direction.

(22) (Nonconfocal Optical System)

In the end face observation device (105-112) according to any one of (10) to (20), the light source and the image capturing element may be arranged at respective positions of different optical distances from the optical element.

(23) (Confocal Optical System)

In the end face observation device (113-122) according to any one of (10) to (20), the light source and the image capturing element may be arranged at respective positions of an equal optical distance from the optical element.

(24) (Light Source and Image Capturing Element Have Optically Conjugate Relationship)

In the end face observation device (113-122) according to any one of (10) to (20), the light source and the image capturing element may be arranged at respective positions which are optically conjugate to the first lens.

(25) (Light Valve)

In the end face observation device (103, 104) according to any one of (1) to (4), the structure (20) may further include an optical member (133) formed from a transparent material other than air and configured to guide illumination light from the light source to the end face of the observation target.

2. Embodiments

Embodiments of an end face observation device according to the present invention will now be described with reference to the accompanying drawings.

<<First Embodiment>>

FIG. 1 is a view showing the arrangement of an end face observation device according to the first embodiment of the present invention.

An end face observation device 101 has a structure in which an observation mechanism configured to observe an end face (an end face of an optical fiber exposed to the center of an optical connector end face) 200A of an optical connector 200 as an observation target and a structure configured to operate the end face 200A of the optical connector 200 are integrated. Note that the optical connector 200 is indicated by an alternate long and two short dashed line in FIG. 1.

A case in which the structure is a cleaning mechanism 13 used to clean the end face 200A of the optical connector 200 will be described below as an example.

More specifically, as shown in FIG. 1, the end face observation device 101 includes an objective lens 12, a cleaning mechanism 13, a light source 9, and an image capturing element 15. The end face observation device 101 has a structure in which the above-described functional elements such as the objective lens 12, the light source 9, and the image capturing element 15 are arranged in, for example, a tubular case 11. The case 11 is filled with, for example, air. The air is a medium that makes light propagate.

Note that a side to arrange the objective lens 12 in the end face observation device 101 in FIG. 1 will be referred to as a "front side", and a side to arrange the light source 9 and the image capturing element 15 in the end face observation device 101 will be referred to as a "rear side" in the following explanation.

The objective lens 12 has a missing portion extending through in the optical axis direction. More specifically, the objective lens 12 has, at the center, a through hole 1200 extending through in the optical axis direction. In other words, the objective lens 12 has a ring shape. The objective lens 12 is arranged at one end of the case 11 such that, for example, its optical axis becomes coaxial with the tubular case 11.

The cleaning mechanism 13 is arranged such that a part can project from the through hole 1200 of the objective lens 12 toward the optical connector 200. As the cleaning mechanism 13, a mechanism having a structure that presses a cleaning tape against the end face of an optical fiber at the center of the optical connector 200 and slides the cleaning tape in a predetermined direction in the end face, as described in patent literature 1, can be exemplified.

FIG. 2A is a view showing a detailed example of the arrangement of the cleaning mechanism 13. FIG. 2A schematically shows a front view of the distal end of the end face observation device 101 viewed from a direction A in FIG. 1.

As shown in FIGS. 1 and 2A, the cleaning mechanism 13 is formed from, for example, a cleaner chip 132 provided in the through hole 1200 of the objective lens 12 and a cleaning tape 131 arranged to partially cover an end face of the cleaner chip 132. The cleaning tape 131 is moved by a sliding mechanism (not shown) in a predetermined direction, for example, in the direction of an arrow in FIG. 2A in the end face of the cleaner chip 132. Note that FIGS. 1 and 2A illustrate not details but only part of the cleaning tape 131 and the cleaner chip 132.

To clean the end face 200A of the optical connector 200, for example, the cleaner chip 132 is made to project from the through hole 1200 of the objective lens 12 toward the optical connector 200 such that the cleaner chip 132 faces the center of the end face 200A of the optical connector 200, and the cleaning tape 131 is pressed against the end face 200A. The cleaning tape 131 is moved in this state, thereby removing foreign substances adhered to the end face 200A.

The image capturing element 15 captures the image of the end face 200A of the optical connector 200 via an optical system, that is the objective lens 12, and generates the image of the end face 200A. The image capturing element 15 can be formed using, for example, a CCD (Charge Coupled Device) or CMOS (Complementary metal-oxide-semiconductor) camera. The image capturing element 15 is arranged on the rear side of the end face observation device 101. More specifically, the image capturing element 15 is mounted on, for example, the surface of a disc-shaped plate member (for example, a substrate) formed in conformity with the shape of a cross section perpendicular to the longitudinal direction of the case 11, and the plate member is arranged at the other end of the case 11.

The light source 9 generates illumination light that irradiates the end face 200A via the objective lens 12. The light source 9 is a light source having a light intensity distribution (luminance) symmetrical with respect to an axis (central axis) passing through its center, and is formed from, for example, an LED or a semiconductor laser.

The light source 9 is arranged to be coaxial with the objective lens 12. More specifically, the central axis of the light source 9 is coaxial with an optical axis 10 of the objective lens 12. Detailed examples of the arrangement of the light source 9 will be described below.

FIG. 2B is a view showing an example of the arrangement of the light source 9. FIG. 2C is a view showing another example of the arrangement of the light source 9. FIGS. 2B and 2C schematically show front views of the distal end of the end face observation device 101 viewed from a direction B in FIG. 1.

As shown in FIG. 2B, the light source 9 has a ring shape. The light source 9 is arranged at the other end of the tubular case 11 so as to be coaxial with the optical axis 10 of the objective lens 12. That is, the light source 9 is arranged at the end of the case 11 on the opposite of the end at which the objective lens 12 is arranged such that a cross section perpendicular to the direction of the central axis of the light source becomes perpendicular to the optical axis 10. The illumination light emitted by the light source 9 thus attains an intensity distribution axisymmetric with respect to the optical axis 10.

As another example of the arrangement of the light source 9, as shown in FIG. 2C, a pair of light sources 9_1 and 9_2 may be arranged so as to be symmetric with respect to the optical axis 10 of the objective lens 12. For example, the pair of light sources 9_1 and 9_2 are arranged at respective positions facing each other via the optical axis 10, that is, on the diameter of the ring. The illumination light emitted by the light sources 9_1 and 9_2 thus attains an intensity distribution axisymmetric with respect to the optical axis 10, as in the case of FIG. 2B.

Note that FIG. 2C illustrates a case in which one set of light sources 9_1 and 9_2 is arranged. However, the present invention is not limited to this, and a plurality of light sources may be arranged on the circumference at equal intervals.

When the light source 9, the objective lens 12, and the image capturing element 15 are arranged in the above-described way, illumination light from the light source 9 and reflected light from the end face 200A propagate through a common space in the case 11. In other words, the illumination light and the reflected light propagate through the same medium (for example, air) in the case 11 along almost the same path. For example, at least some components of the illumination light from the light source 9 propagate in the case 11 and are guided to the end face 200A of the optical connector 200 via an annular portion 1201 of the objective lens 12. On the other hand, at least some components of the reflected light from the end face 200A of the optical connector 200 pass through the annular portion 1201 of the objective lens 12, propagate in the case 11, and form an image on the image capturing element 15.

FIG. 3A is a view for explaining a method of using the end face observation device according to the first embodiment. FIG. 3A shows a state in which the end face of an optical connector having a receptacle shape is observed by the end face observation device 101. In the optical connector having the receptacle shape, the optical connector main body 200 is arranged in a tubular member called a split sleeve 201.

As shown in FIG. 3A, the end face observation device 101 is designed such that an outermost diameter L1 of the distal end of the end face observation device 101 becomes equal to or smaller than a connector inner diameter L2. Since the user can thus insert the end face observation device 101 into the split sleeve 201, cleaning and observation of the end face 200A of the optical connector 200 are possible. When the outermost diameter of the distal end of the end face observation device 101 is made equal to or smaller than the connector inner diameter, as described above, cleaning and observation by one end face observation device can be performed for any optical connector having a receptacle shape or a plug shape.

Figure 3B:
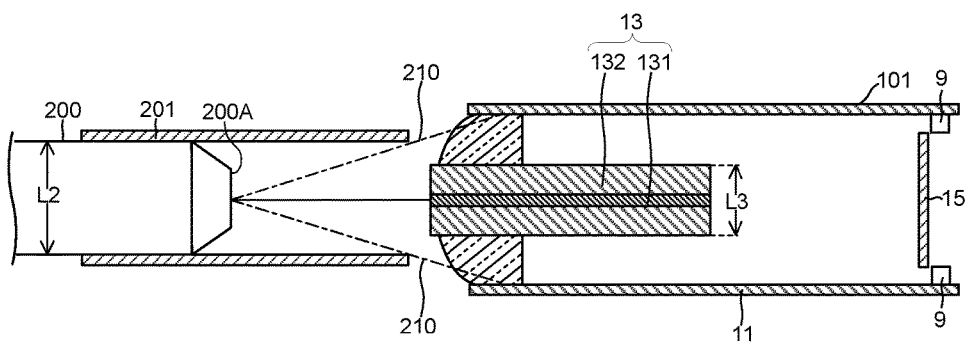
FIG. 3B is a view for explaining another method of using the end face observation device according to the first embodiment.

FIG. 3B is a view for explaining another method of using the end face observation device according to the first embodiment. FIG. 3B shows a state in which the end face of an optical connector having a receptacle shape is observed by the end face observation device 101. As shown in FIG. 3B, the end face observation device observes the end face in a state in which the device is arranged outside the split sleeve 201. The end face observation device 101 is designed such that an outermost diameter L3 of the distal end of the cleaning mechanism 13 becomes equal to or smaller than the connector inner diameter L2.

Since the user can thus insert the cleaning mechanism 13 into the split sleeve 201, cleaning and observation of the end face 200A of the optical connector 200 are possible.

In addition, when the shape of the objective lens 12 is designed such that the opening of the objective lens 12 becomes larger than an opening (an alternate long and short dashed line 210 shown in FIG. 3B) decided by the end face position of the optical connector having the receptacle shape and the length of the split sleeve 201, a high-resolution image can be observed without a loss in the observed image or darkening of the peripheral portion of the observed image.

As described above, according to the end face observation device of the first embodiment, part of the cleaning mechanism is arranged in the missing portion of the objective lens, thereby integrating the cleaning device and the observation device for the end face of the optical connector. Accordingly, when, for example, connecting the optical connector, images before and after cleaning of the end face can be observed. For this reason, the cleaning device and the observation device need not be prepared separately. Hence, according to the end face observation device of the first embodiment, the operation is easy, and the operation time can be shortened.

In addition, according to the end face observation device 101 of the first embodiment, since the light source 9 and the objective lens 12 are arranged coaxially with the optical axis 10, it is possible to construct a coaxial optical system in which both the intensity distribution of illumination light generated by the light source 9 and the intensity distribution of reflected light from the end face 200A of the optical connector 200 are axisymmetric with respect to the optical axis. In other words, a coaxial optical system in which the center of the intensity of the illumination light and the center of the intensity of the reflected light from the end face are located near the optical axis can be constructed. It is therefore possible to suppress unevenness of illumination for the end face 200A of the optical connector 200 and obtain a uniform image of the end face 200A with little unevenness.

Furthermore, according to the end face observation device 101 of the first embodiment, the light propagation path of the illumination light and the light propagation path of the reflected light are not separated from each other. For this reason, it is unnecessary to provide different media for the light propagation paths, and an increase in the number of components or an increase in the manufacturing cost can be suppressed.

Note that when the objective lens 12 is provided with a missing portion, the brightness or contrast of an image may lower. However, for example, by appropriately designing the area of the missing portion of the objective lens 12 and the lens opening of the objective lens 12, an observed image in which degradation in the image resolution is suppressed can be formed on the image capturing element 15.

<<Second Embodiment>>

Figure 4:
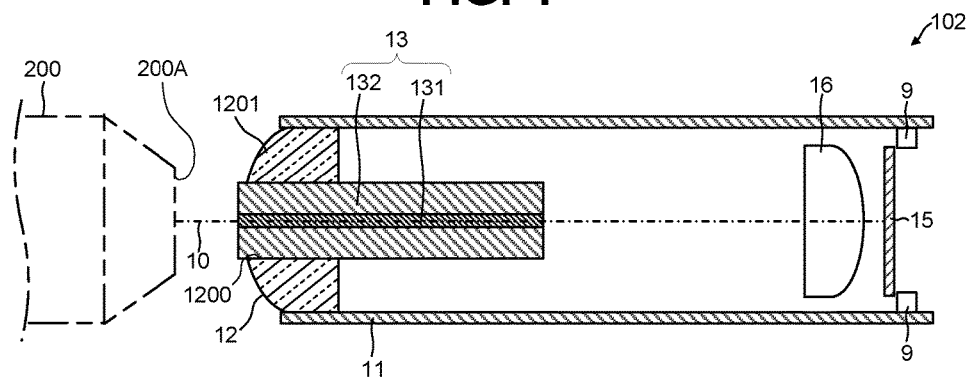
FIG. 4 is a view showing an arrangement of an end face observation device according to the second embodiment.

FIG. 4 is a view showing the arrangement of an end face observation device according to the second embodiment.

An end face observation device 102 shown in FIG. 4 is different from the end face observation device 101 according to the first embodiment in that a lens 16 is further provided between an objective lens 12 and an image capturing element 15. The rest of the arrangement is the same as the end face observation device 101. In the following explanation, the same reference numerals as in the end face observation device 101 according to the first embodiment denote common constituent elements, and a detailed description thereof will be omitted.

The lens 16 provided between the objective lens 12 and the image capturing element 15 has a focal length different from that of the objective lens 12. Hence, the magnification of an image formed on the image capturing element 15 can be adjusted by adjusting the ratio of the focal length of the lens 16 to the focal length of the objective lens 12.

As described above, according to the end face observation device of the second embodiment, since the lens 16 is provided between the objective lens 12 and the image capturing element 15, the magnification of an image formed on the image capturing element can be adjusted by adjusting the ratio of the focal length of the lens 16 to the focal length of the objective lens 12. The resolution of the image formed on the imaging plane of the image capturing element 15 can thus be improved. In addition, since the magnification of the image can be adjusted, the length of a tubular case 11 can be increased, and the design freedom of the end face observation device increases.

In addition, according to the end face observation device of the second embodiment, when an end face 200A of an optical connector 200 is arranged at the focal position of the objective lens 12, reflected light (the image of the end face 200A) from the end face 200A of the optical connector 200 propagates as almost parallel light between the objective lens 12 and the lens 16 in the case 11. For this reason, even if an obstacle such as a cleaning mechanism 13 exists at the center of the objective lens 12, a high-definition image can be formed on the imaging plane of the image capturing element 15. This facilitates detecting, for example, the size of a foreign substance adhered to the optical connector end face.

Note that in the end face observation device 102, a transparent member 17 may be provided between the objective lens 12 and the lens 16, as shown in FIG. 5, to construct an optical system that avoids an obstacle such as a cleaning mechanism, as described above. For example, when a lens is provided as the transparent member 17, the optical design freedom further increases, and an obstacle can be avoided more easily, as compared to an optical system including two lenses, that is, the objective lens 12 and the lens 16. This can improve optical performance by, for example, suppressing a chromatic aberration and coma and obtain an image of higher quality.

<<Third Embodiment>>

FIG. 6 is a view showing the arrangement of an end face observation device according to the third embodiment.

An end face observation device 103 shown in FIG. 6 is different from the end face observation device 102 according to the second embodiment in that the end face observation device includes a deflecting mirror 18 that reflects illumination light from a light source, and a light valve 133 that is provided in a through hole 1200 of an objective lens 12 and illuminates an end face 200A of an optical connector 200 by mainly making the light reflected by the deflecting mirror 18 propagate. The rest of the arrangement is the same as the end face observation device 102. In the following explanation, the same reference numerals as in the end face observation device 102 according to the second embodiment denote common constituent elements, and a detailed description thereof will be omitted.

More specifically, in the end face observation device 103, for example, an opening is provided at part of a tubular case 11, and a light source 14 is provided outside the opening, as shown in FIG. 6. The light source 14 is a single light source and is formed from, for example, an LED or a semiconductor laser. The end face observation device 103 also includes the deflecting mirror 18 and a light shielding plate 19. The deflecting mirror 18 is an optical component used to change the propagation direction of illumination light emitted by the light source 14. The light shielding plate 19 is an optical component that blocks light, and is placed to cover part of the light valve 133 and the deflecting mirror 18 not to make reflected light from the end face 200A which propagates through the light valve 133 propagate up to an image capturing element 15.

Additionally, in place of the cleaning mechanism 13, the end face observation device 103 includes a cleaning mechanism 20 with a cleaner chip partially formed from the light valve 133. The light valve 133 is a member that is made of a transparent material other than air and guides the illumination light from the light source 14 to the end face 200A of the optical connector 200.

In the end face observation device 103, the illumination light from the light source 14 is deflected by the deflecting mirror 18, mainly propagates in the light valve 133 provided in the through hole 1200 of the objective lens 12, and is guided to the end face 200A of the optical connector 200. On the other hand, the reflected light from the end face 200A of the optical connector 200 passes through an annular portion 1201 of the objective lens 12 and the light valve 133 and propagates in the case 11. At this time, the reflected light from the end face 200A which has passed through the light valve 133 is blocked by the light shielding plate 19 and does not propagate to the image capturing element 15. For this reason, the reflected light from the end face 200A, which has passed through the annular portion 1201 of the objective lens 12, mainly forms an image on the imaging plane of the image capturing element 15 via the lens 16.

According to the end face observation device of the third embodiment, since the illumination light from the light source is guided to the end face 200A of the optical connector 200 via the light valve 133 provided in the through hole of the objective lens 12, the end face 200A can be irradiated with the illumination light more evenly in a wider range as compared to a case in which the illumination light propagates in air.

In addition, even if the single light source is used, an even illumination light distribution can be obtained. For this reason, a plurality of light sources need not be provided, and the number of components can be decreased.

Furthermore, by providing the light shielding plate 19 so as not to make the reflected light from the end face which has propagated in the light valve 133 propagate up to the image capturing element, degradation in the resolution which occurs when the reflected light that has propagated in the light valve 133 reaches the image capturing element 15 can be prevented. It is therefore possible to obtain an image of a higher resolution on the image capturing element 15.

Note that in the end face observation device 103 according to the third embodiment, the light valve is used. However, the same effect as described above can be obtained by intervention of, for example, a fiber bundle or a diffuser in place of the light valve. Additionally, when the illumination light propagates through the space in the through hole of the objective lens 12, propagation can be performed at a higher efficiency.

<<Fourth Embodiment>>

FIG. 7 is a view showing the arrangement of an end face observation device according to the fourth embodiment.

An end face observation device 104 shown in FIG. 7 is different from the end face observation device 103 according to the third embodiment in that a single light source 14 is arranged near a light valve 133. The rest of the arrangement is the same as the end face observation device 103. In the following explanation, the same reference numerals as in the end face observation device 103 according to the third embodiment denote common constituent elements, and a detailed description thereof will be omitted.

As shown in FIG. 7, in the end face observation device 104, the light source 14 is arranged near an end of the light valve 133 on the side opposite to the side inserted into an objective lens 12. In addition, a light shielding plate 21 is arranged on the periphery of the light source 14 not to make reflected light that has propagated in the light valve reach an image capturing element 15.

As described above, according to the end face observation device of the fourth embodiment, an end face can be irradiated with illumination light from the light source more evenly in a wider range, and an image of a higher resolution can be obtained on the image capturing element 15, as in the end face observation device according to the third embodiment.

In addition, even if the single light source is used, an even illumination light distribution can be obtained. For this reason, a plurality of light sources need not be provided, and the number of components can be decreased.

Furthermore, according to the end face observation device of the fourth embodiment, since the propagation direction of the illumination light from the light source need not be changed, the number of components can be decreased, and the end face observation device can be made compact.

<<Fifth Embodiment>>

Figure 8:
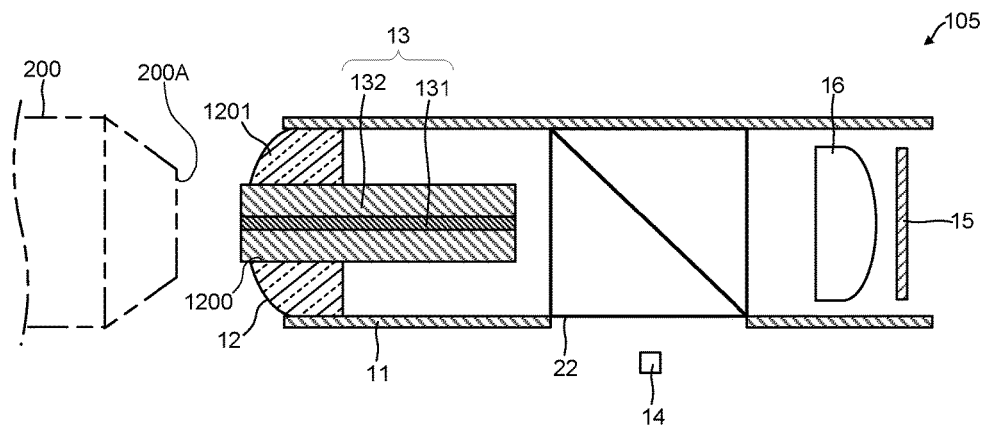
FIG. 8 is a view showing the arrangement of an end face observation device according to the fifth embodiment.

FIG. 8 is a view showing the arrangement of an end face observation device according to the fifth embodiment.

An end face observation device 105 shown in FIG. 8 is different from the end face observation device 102 according to the second embodiment in that illumination light from a light source 14 arranged outside a tubular case 11 is reflected by an optical element such as a beam splitter, and reflected light from an end face of an optical connector is made to pass through the optical element and propagate up to an image capturing element. The rest of the arrangement is the same as the end face observation device 102. In the following explanation, the same reference numerals as in the end face observation device 102 according to the second embodiment denote common constituent elements, and a detailed description thereof will be omitted.

More specifically, the end face observation device 105 further includes an optical element 22.

The optical element 22 is provided on the optical axis between an objective lens 12 and an image capturing element 15. The optical element 22 is an optical component that partially reflects incident light and partially passes the incident light and is, for example, a beam splitter or a half mirror. In the following explanation, the optical element 22 is assumed to be a beam splitter as an example, and the optical element 22 will be referred to as the beam splitter 22.

The light source 14 is arranged, for example, outside the tubular case 11. More specifically, for example, an opening is provided at part of the tubular case 11, and the light source 14 is arranged outside the opening, as shown in FIG. 8.

Here, the light source 14 may be arranged in a place deviated from the confocal point of the end face of an observation target. For example, the light source 14 and the image capturing element 15 may be arranged at respective positions of different optical distances from the beam splitter 22 such that the image of the light source 14 is formed in the missing portion of the objective lens 12. Alternatively, the light source 14 and the image capturing element 15 may be arranged at respective positions of different optical distances from the beam splitter 22 such that the image of the light source is formed in front of an end face 200A of an optical connector 200.

When the end face observation device 105 is configured in the above-described way, light propagates in the following way. For example, light generated by the light source 14 is reflected by the beam splitter 22, transmitted through the objective lens 12, and irradiates the end face 200A of the optical connector 200. On the other hand, reflected light from the end face 200A of the optical connector 200 passes through the objective lens 12, the beam splitter 22, and a lens 16 in this order and forms an image on the imaging plane of the image capturing element 15.

As described above, according to the end face observation device of the fifth embodiment, the beam splitter is provided, thereby easily constructing, at a position in front of the beam splitter, a coaxial optical system in which both the intensity distribution of illumination light from the light source and the intensity distribution of reflected light from the end face of the observation target are axisymmetric with respect to the optical axis. In other words, a coaxial optical system in which the center of the intensity of the illumination light and the center of the intensity of the reflected light from the end face are located near the optical axis can easily be constructed at a position between the objective lens 12 and the beam splitter 22. Accordingly, even if the single light source is used, an even illumination light distribution can be obtained. For this reason, a plurality of light sources need not be provided, and the number of components can be decreased. In addition, when the coaxial optical system is constructed in the above-described way, it is possible to suppress unevenness of the illumination light and obtain a high-resolution image of the end face of the observation target with little unevenness, as in the end face observation device according to the first embodiment.

In addition, according to the end face observation device of the fifth embodiment, restrictions on the place to arrange the light source decrease, and the layout design is facilitated, as compared to a case in which an optical element such as a beam splitter or a half mirror is not used.

Furthermore, in the end face observation device according to the fifth embodiment, a more even illumination light distribution and an image of a higher resolution can be obtained by arranging the light source at a position deviated from the confocal point of the end face of the observation target, as compared to a case in which a confocal arrangement is employed. For example, when the light source is arranged at the confocal point of the end face of the observation target, the image of the light source and the image of the end face of the observation target overlap, and the evenness of illumination light or the image quality of reflected light (image light) from the end face may thus degrade. Since this problem can be prevented by arranging the light source at a position deviated from the confocal point of the end face of the observation target, a more even illumination light distribution and an image of a higher resolution can be obtained.

In particular, when the light source 14 and the image capturing element 15 are arranged at respective positions of different optical distances from the beam splitter 22 such that the image of the light source is formed in front of the end face 200A of the optical connector 200, the degree of illumination light blocking by a structure 13 arranged in the missing portion of the objective lens 12 lowers. It is therefore possible to obtain brighter illumination light.

In addition, in the end face observation device according to the fifth embodiment, when a lens 16 is arranged between the image capturing element 15 and the beam splitter 22, an optical system configured to form the image of reflected light from the end face 200A of the optical connector 200 can be designed separately from an optical system for the illumination light from the light source 14. It is possible to make design considering, for example, the characteristic of directivity of the light source 14 and facilitate optical design to obtain an image of a higher resolution.

<<Sixth Embodiment>>

Figure 9A:
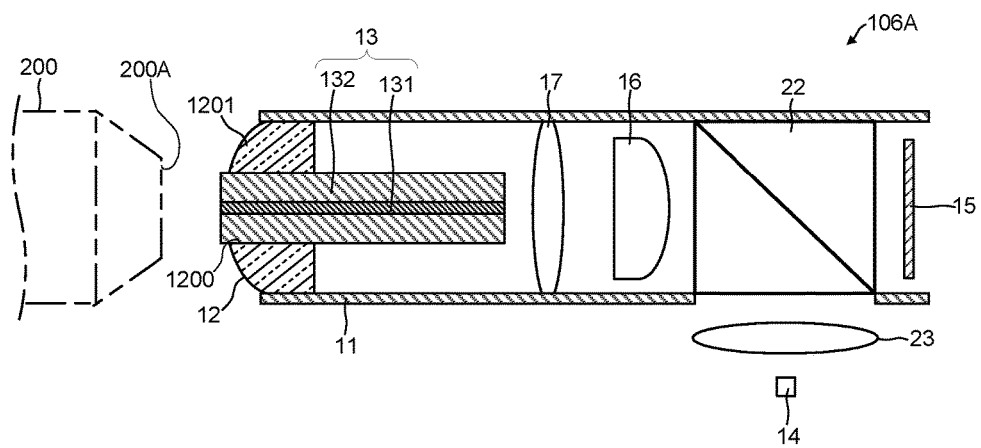
FIG. 9A is a view showing an arrangement of an end face observation device according to the sixth embodiment.
Figure 9B:
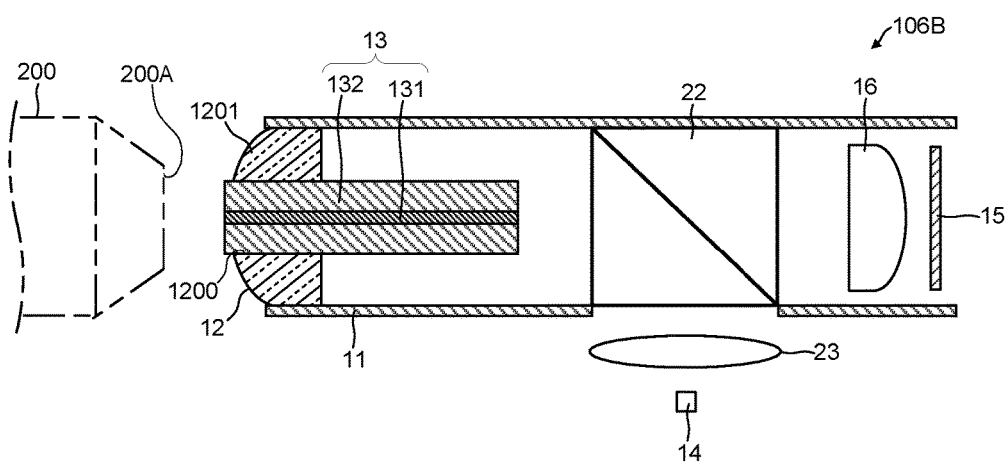
FIG. 9B is a view showing another arrangement of the end face observation device according to the sixth embodiment.
Figure 9C:
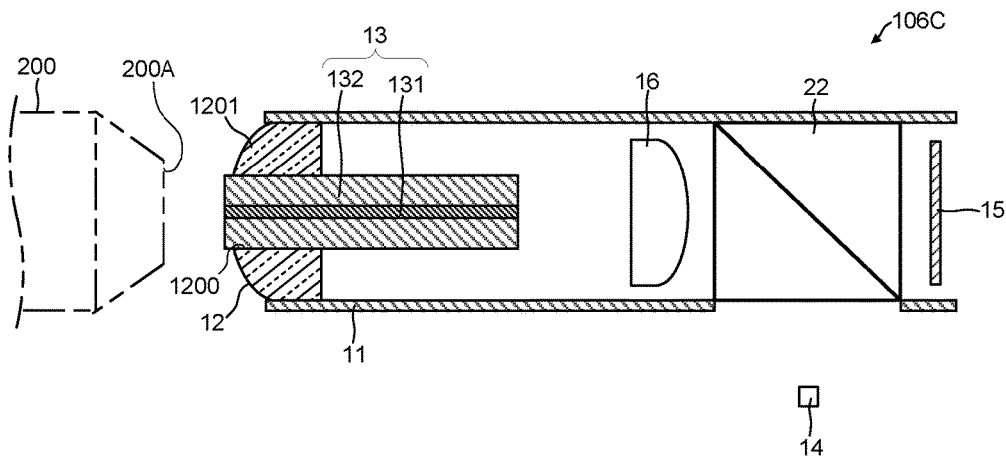
FIG. 9C is a view showing still another arrangement of the end face observation device according to the sixth embodiment.
Figure 9D:
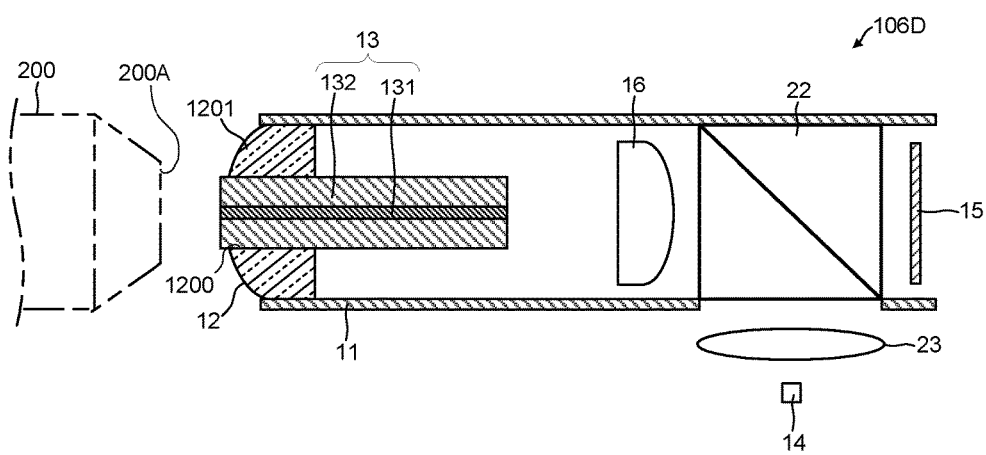
FIG. 9D is a view showing yet another arrangement of the end face observation device according to the sixth embodiment.
Figure 9E:
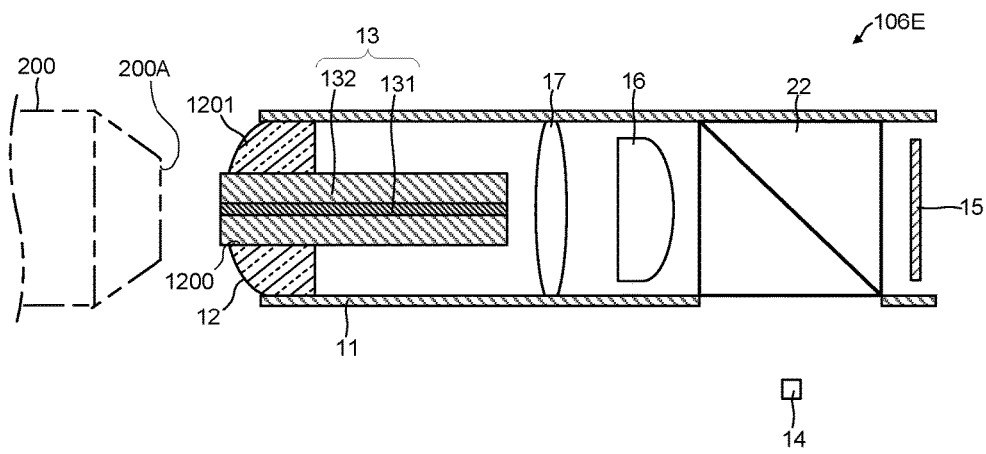
FIG. 9E is a view showing still yet another arrangement of the end face observation device according to the sixth embodiment.

FIG. 9A is a view showing the arrangement of an end face observation device according to the sixth embodiment.

An end face observation device 106A shown in FIG. 9A is a modification of the end face observation device 105 according to the fifth embodiment. In the following explanation, the same reference numerals as in the end face observation device 105 according to the fifth embodiment denote common constituent elements, and a detailed description thereof will be omitted.

More specifically, the end face observation device 106A includes a lens 23 between a beam splitter 22 and a light source 14. The end face observation device 106A also includes, between the beam splitter 22 and an objective lens 12, a lens 16 and a lens-shaped transparent member 17 which constitute a lens system common to illumination light from the light source 14 and reflected light (image light) from an end face 200A. The end face observation device 106A includes no lens system between an image capturing element 15 and the beam splitter 22.

According to the end face observation device 106A of the sixth embodiment, since the lens 23 is provided between the beam splitter 22 and the light source 14, an optical system for the illumination light from the light source 14 can be designed separately from an optical system configured to form the image of the reflected light from the end face 200A of an optical connector 200. It is possible to make design considering, for example, the characteristic of directivity of the light source 14 and provide high-quality illumination light.

In addition, according to the end face observation device 106A of the sixth embodiment, since the lens 16 and the lens-shaped transparent member 17 are provided between the beam splitter 22 and the objective lens 12, the illumination light and the reflected light can share the optical components such as a lens. This can decrease the number of components and attain effects such as easy assembly and cost reduction.

Furthermore, according to the end face observation device 106A of the sixth embodiment, since no lens system is provided between the image capturing element 15 and the beam splitter 22, the light source 14 and the image capturing element 15 can be arranged in closer vicinity. This can aggregate the power supply units (not shown) of the image capturing element 15 and the light source 14 and reduce the size of the end face observation device.

Note that FIG. 9A shows a case in which all of three characteristic arrangements, that is, providing the lens 23 between the beam splitter 22 and the light source 14, providing at least one of the lens 16 and the transparent member 17 between the beam splitter 22 and the objective lens 12, and providing no lens system between the image capturing element 15 and the beam splitter 22 are included. However, the present invention is not limited to this. For example, the three characteristic arrangements may appropriately be combined, as in end face observation devices 106B to 106E shown in FIGS. 9B to 9E.

<<Seventh Embodiment>>

FIG. 10 is a view showing the arrangement of an end face observation device according to the seventh embodiment.

An end face observation device 107 shown in FIG. 10 is different from the end face observation device 105 according to the fifth embodiment in that a lens 16 is provided between an objective lens 12 and a beam splitter 22, and a light amount adjustment mechanism is provided near an image capturing element 15. The rest of the arrangement is the same as the end face observation device 105. In the following explanation, the same reference numerals as in the end face observation device 105 according to the fifth embodiment denote common constituent elements, and a detailed description thereof will be omitted.

More specifically, the lens 16 is arranged not between the beam splitter 22 and the image capturing element 15 but between the objective lens 12 and the beam splitter 22. The lens 16 is a lens with a focal length different from that of the objective lens 12.

Additionally, the end face observation device 107 includes a light amount adjustment mechanism (to be referred to as an "iris" hereinafter) 24 between the beam splitter 22 and the image capturing element 15. The iris 24 is, for example, a plate-shaped member with an opening. The iris 24 blocks incident light from outside of the opening to the image capturing element 15 and limits the image receiving plane of the image capturing element 15.

When the iris 24 is arranged, light (stray light) that enters from a path different from the expected propagation path of reflected light (image light) from an end face 200A to the image capturing element 15 can be removed.

As described above, according to the end face observation device 107 of the seventh embodiment, the iris 24 is provided in the above-described way, thereby reducing degradation in image quality caused by stray light and improving the quality of an image.

<<Eighth Embodiment>>

FIG. 11 is a view showing the arrangement of an end face observation device according to the eighth embodiment.

An end face observation device 108 shown in FIG. 11 is different from the end face observation device 107 according to the seventh embodiment in that an iris 25 is provided between a light source 14 and a beam splitter 22. The rest of the arrangement is the same as the end face observation device 107. In the following explanation, the same reference numerals as in the end face observation device 107 according to the seventh embodiment denote common constituent elements, and a detailed description thereof will be omitted.

More specifically, the end face observation device 108 includes the iris 25 between the light source 14 and the beam splitter 22. Incident light on the beam splitter 22 can thus be limited. It is therefore possible to suppress generation of stray light resulted from unexpected light such as reflected light on the periphery of the beam splitter 22 or direct incident light from the light source 14 to an image capturing element 15 and reduce unwanted stray light other than reflected light that enters from an end face 200A to the image capturing element 15.

As described above, according to the end face observation device 108 of the eighth embodiment, the iris 25 is provided in the above-described way, thereby reducing degradation in image quality caused by stray light and improving the quality of an image.

Note that in the end face observation device 108 according to the eighth embodiment, an iris 24 may further be provided between the beam splitter 22 and the image capturing element 15, as in the end face observation device 107 according to the seventh embodiment.

<<Ninth Embodiment>>

FIG. 12 is a view showing the arrangement of an end face observation device according to the ninth embodiment.

An end face observation device 109 shown in FIG. 12 is different from the end face observation device 107 according to the seventh embodiment in that a wavelength filter 26 is provided between a beam splitter 22 and an image capturing element 15. The rest of the arrangement is the same as the end face observation device 107. In the following explanation, the same reference numerals as in the end face observation device 107 according to the seventh embodiment denote common constituent elements, and a detailed description thereof will be omitted.

More specifically, the wavelength filter 26 provided between the beam splitter 22 and the image capturing element 15 is an optical filter that passes light in a predetermined wavelength range and absorbs or reflects light in remaining wavelength ranges. This can limit the wavelength range of incident light on the image capturing element 15 and reduce blurs of image light caused by a chromatic aberration.

As described above, according to the end face observation device 109 of the ninth embodiment, the wavelength filter 26 is provided in the above-described way, thereby limiting the wavelength range of incident light on the image capturing element 15 and reducing blurs of image light caused by a chromatic aberration. It is therefore possible to reduce degradation in image quality and improve the quality of an image.

<<10th Embodiment>>

Figure 13:
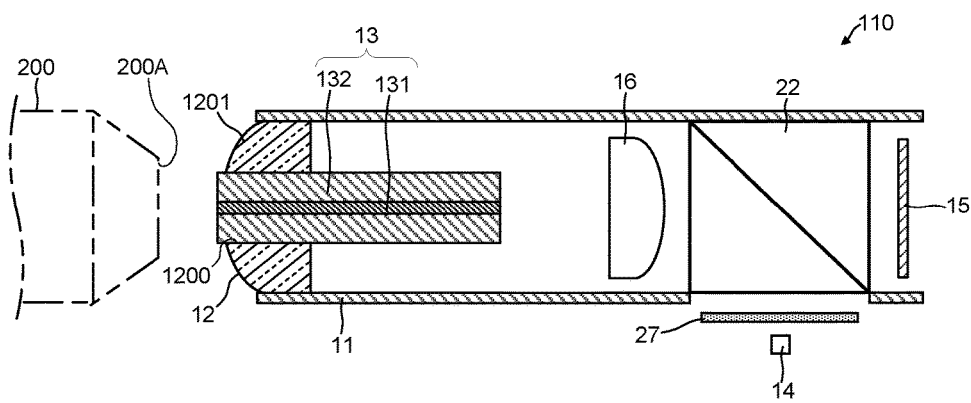
FIG. 13 is a view showing the arrangement of an end face observation device according to the 10th embodiment.

FIG. 13 is a view showing the arrangement of an end face observation device according to the 10th embodiment.

An end face observation device 110 shown in FIG. 13 is different from the end face observation device 109 according to the ninth embodiment in that a wavelength filter 27 is provided between a light source 14 and a beam splitter 22. The rest of the arrangement is the same as the end face observation device 109. In the following explanation, the same reference numerals as in the end face observation device 109 according to the ninth embodiment denote common constituent elements, and a detailed description thereof will be omitted.

More specifically, the wavelength filter 27 provided between the light source 14 and the beam splitter 22 limits the wavelength range of illumination light from the light source 14. It is consequently possible to suppress the influence of the chromatic aberration of an optical system.

As described above, according to the end face observation device 110 of the 10th embodiment, the wavelength filter 27 is provided in the above-described way, thereby limiting the wavelength range of the illumination light from the light source 14 and suppressing the influence of the chromatic aberration of the optical system. It is therefore possible to improve the quality of an image formed on an image capturing element 15.

Note that in the end face observation device 110 according to the 10th embodiment, a wavelength filter 26 may further be provided between the beam splitter 22 and the image capturing element 15, as in the end face observation device 109 according to the ninth embodiment.

<<11th Embodiment<<

Figure 14:
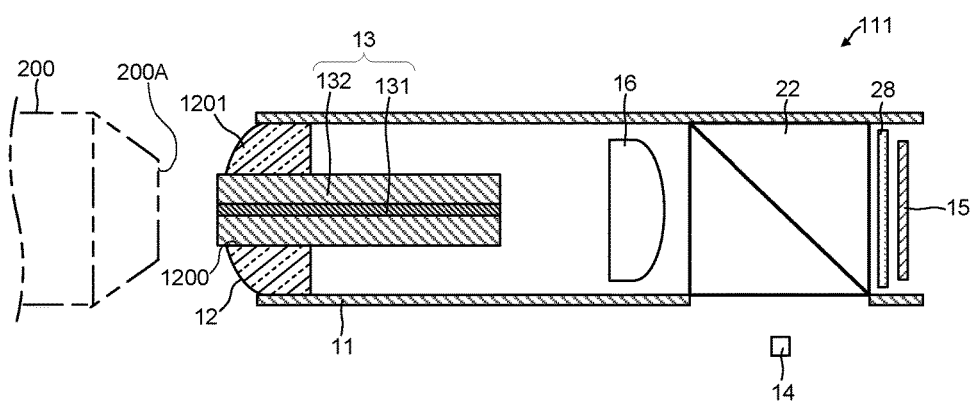
FIG. 14 is a view showing the arrangement of an end face observation device according to the 11th embodiment.

FIG. 14 is a view showing the arrangement of an end face observation device according to the 11th embodiment.

An end face observation device 111 shown in FIG. 14 is different from the end face observation device 109 according to the ninth embodiment in that a polarization filter 28 is provided between a beam splitter 22 and an image capturing element 15. The rest of the arrangement is the same as the end face observation device 109. In the following explanation, the same reference numerals as in the end face observation device 109 according to the ninth embodiment denote common constituent elements, and a detailed description thereof will be omitted.

More specifically, the polarization filter 28 provided between the beam splitter 22 and the image capturing element 15 is an optical filter that passes light in a predetermined polarization direction and absorbs or reflects light in remaining polarization directions. This can limit the polarization direction of incident light on the image capturing element 15 and reduce blurs of image light caused by the polarization dependence of an optical component.

As described above, according to the end face observation device 111 of the 11th embodiment, the polarization filter 28 is provided in the above-described way, thereby limiting the polarization direction of incident light on the image capturing element 15 and reducing blurs of image light caused by the polarization dependence of an optical component. It is therefore possible to reduce degradation in image quality and improve the quality of an image.

<<12th Embodiment>>

Figure 15:
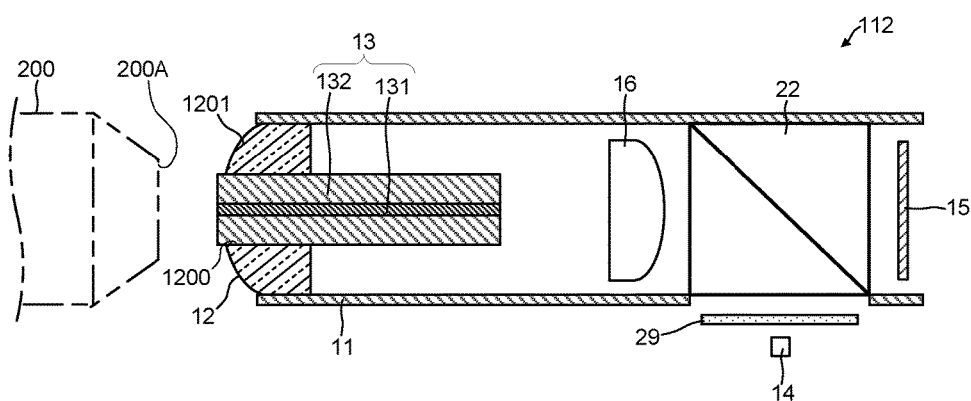
FIG. 15 is a view showing the arrangement of an end face observation device according to the 12th embodiment.

FIG. 15 is a view showing the arrangement of an end face observation device according to the 12th embodiment.

An end face observation device 112 shown in FIG. 15 is different from the end face observation device 111 according to the 11th embodiment in that a polarization filter 29 is provided between a light source 14 and a beam splitter 22. The rest of the arrangement is the same as the end face observation device 111. In the following explanation, the same reference numerals as in the end face observation device 111 according to the 11th embodiment denote common constituent elements, and a detailed description thereof will be omitted.

More specifically, the polarization filter 29 provided between the light source 14 and the beam splitter 22 limits the polarization direction of illumination light from the light source 14. It is consequently possible to suppress the influence of the polarization dependence of an optical system.

As described above, according to the end face observation device 112 of the 12th embodiment, the polarization filter 29 is provided in the above-described way, thereby limiting the polarization direction of the illumination light from the light source 14 and suppressing the influence of the polarization dependence of the optical system. It is therefore possible to improve the quality of an image formed on an image capturing element 15.

Note that in the end face observation device 112 according to the 12th embodiment, a polarization filter 28 may further be provided between the beam splitter 22 and the image capturing element 15, as in the end face observation device 111 according to the 11th embodiment.

<<13th Embodiment>>

Figure 16:
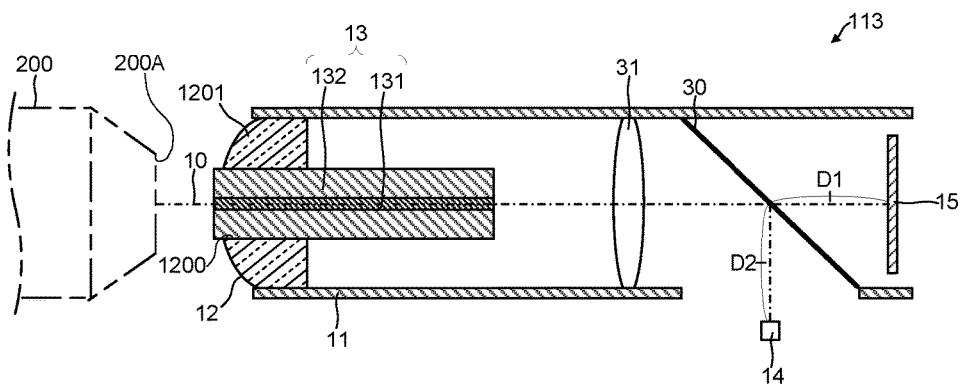
FIG. 16 is a view showing the arrangement of an end face observation device according to the 13th embodiment.

FIG. 16 is a view showing the arrangement of an end face observation device according to the 13th embodiment.

An end face observation device 113 shown in FIG. 16 is different from the end face observation devices 105 to 112 according to the fifth to 12th embodiments in that a light source 14 is arranged at the position of the confocal point of an end face of an observation target. The rest of the arrangement is the same as the end face observation devices 105 to 112. In the following explanation, the same reference numerals as in the end face observation devices 105 to 112 according to the fifth to 12th embodiments denote common constituent elements, and a detailed description thereof will be omitted.

More specifically, the end face observation device 113 includes an objective lens 12, a cleaning mechanism 13, a lens 31, an image capturing element 15, the light source 14, and an optical element 30 in, for example, a tubular case 11, as shown in FIG. 16.

The optical element 30 is provided on the optical axis between the objective lens 12 and the image capturing element 15. The optical element 30 is an optical component that partially reflects incident light and partially passes the incident light and is, for example, a beam splitter or a half mirror. In the following explanation, the optical element 30 is assumed to be a half mirror as an example, and the optical element 30 will be referred to as the half mirror 30. The ratio of reflected light and transmitted light by the half mirror 30 is, for example, 1:1.

The lens 31 is arranged between the half mirror 30 and the objective lens 12, and constitutes a lens system common to illumination light from the light source 14 and reflected light (image light) from an end face 200A.

The image capturing element 15 is arranged on the optical axis of the lens 31. The light source 14 is arranged while being spaced part from, for example, the half mirror 30 in a direction perpendicular to the optical axis of the lens 31.

Here, a distance D1 between the half mirror 30 and the image capturing element 15 and a distance D2 between the half mirror 30 and the light source 14 optically equal. Additionally, in an optical system having the objective lens 12 at one end (front end) and the lens 31 at the other end (rear end), the image capturing element 15 is arranged at the focal position of the rear end, and the light source 14 is arranged at the focal position of the rear end via the half mirror 30. That is, the light source 14 and the half mirror 30 are arranged near the image capturing element 15 such that the light source 14 and the image capturing element 15 hold an optically conjugate positional relationship with respect to the objective lens 12.

Hence, when the end face 200A of an optical connector 200 is arranged at the focal position of the front end of the optical system, the end face 200A of the optical connector 200, the image capturing element 15, and the light source 14 attain an optically conjugate positional relationship, and the end face observation device 113 implements a confocal optical system.

According to the above-described optical system, light propagates in the following way. For example, light generated by the light source 14 is reflected by the half mirror 30, transmitted through the lens 31 and an annular portion 1201 of the objective lens 12, and irradiates the end face 200A of the optical connector 200. On the other hand, reflected light (image light) from the end face 200A of the optical connector 200 passes through the annular portion 1201 of the objective lens 12, the lens 31, and the half mirror 30 in this order and forms an image on the imaging plane of the image capturing element 15.

As described above, according to the end face observation device 113 of the 13th embodiment, the light source 14 and the image capturing element 15 are arranged at respective positions which are optically conjugate to the objective lens 12, thereby arranging the light source 14 and the imaging plane of the image capturing element 15 in close vicinity. This can aggregate, for example, the power supply unit (not shown) that supplies power to the image capturing element 15 and the light source 14 and reduce the size of the end face observation device.

<<14th Embodiment>>

Figure 17:
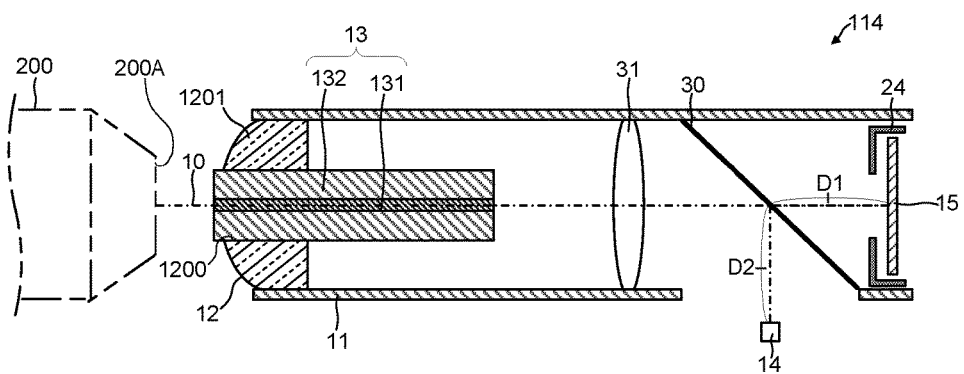
FIG. 17 is a view showing the arrangement of an end face observation device according to the 14th embodiment.

FIG. 17 is a view showing the arrangement of an end face observation device according to the 14th embodiment.

An end face observation device 114 shown in FIG. 17 is different from the end face observation device 113 according to the 13th embodiment in that an iris 24 is provided between a half mirror 30 and an image capturing element 15. The rest of the arrangement is the same as the end face observation device 113. In the following explanation, the same reference numerals as in the end face observation device 113 according to the 13th embodiment denote common constituent elements, and a detailed description thereof will be omitted.

More specifically, in the end face observation device 114, the iris 24 provided between the half mirror 30 and the image capturing element 15 removes stray light that enters from a path different from a normal path to the image capturing element 15, as in the end face observation device 107 according to the seventh embodiment.

As described above, according to the end face observation device 114 of the 14th embodiment, the size can be reduced, as in the end face observation device 113 according to the 13th embodiment. In addition, the iris 24 is provided in the above-described way, thereby reducing degradation in image quality caused by stray light and improving the quality of an image, as in the end face observation device 107 according to the seventh embodiment.

<<15th Embodiment>>

Figure 18:
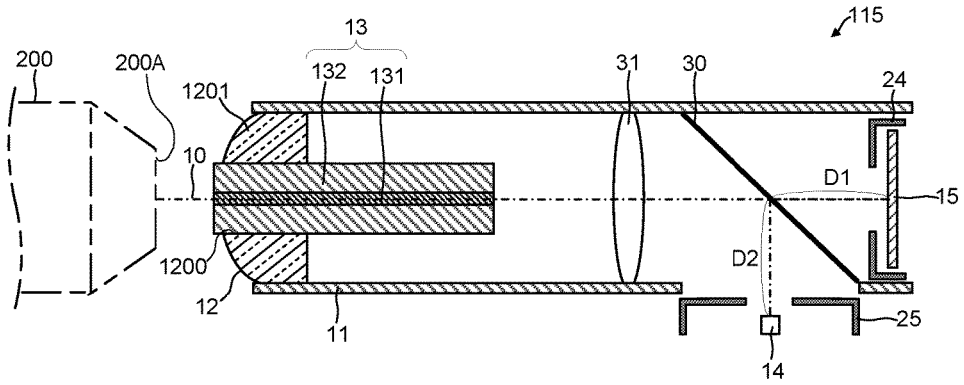
FIG. 18 is a view showing the arrangement of an end face observation device according to the 15th embodiment.

FIG. 18 is a view showing the arrangement of an end face observation device according to the 15th embodiment.

An end face observation device 115 shown in FIG. 18 is different from the end face observation device 114 according to the 14th embodiment in that an iris 25 is provided between a half mirror 30 and a light source 14. The rest of the arrangement is the same as the end face observation device 114. In the following explanation, the same reference numerals as in the end face observation device 114 according to the 14th embodiment denote common constituent elements, and a detailed description thereof will be omitted.

More specifically, the iris 25 provided between the half mirror 30 and the light source 14 removes unwanted light that enters the half mirror 30, as in the end face observation device 108 according to the eighth embodiment. This can reduce unwanted stray light (for example, reflected light on the periphery of the half mirror 30 or light that directly enters from the light source 14 to an image capturing element 15) other than reflected light that enters from an end face 200A to the image capturing element 15.

As described above, according to the end face observation device 115 of the 15th embodiment, the iris 25 is provided in the above-described way, thereby further improving the quality of an image.

<<16th Embodiment>>

Figure 19:
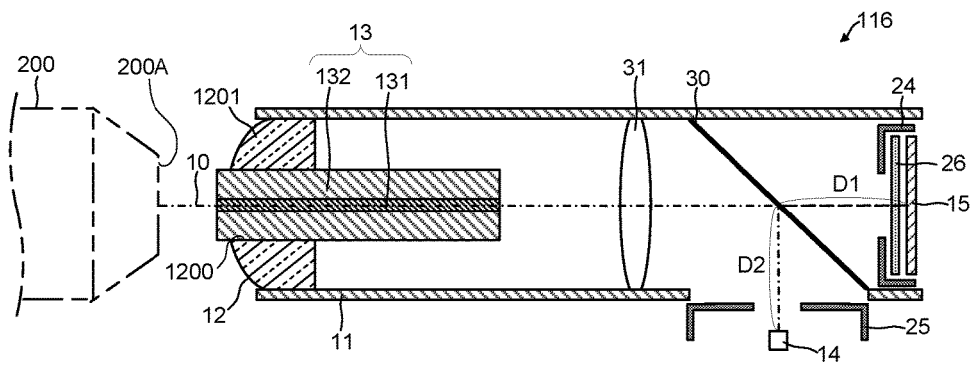
FIG. 19 is a view showing the arrangement of an end face observation device according to the 16th embodiment.

FIG. 19 is a view showing the arrangement of an end face observation device according to the 16th embodiment.

An end face observation device 116 shown in FIG. 19 is different from the end face observation device 115 according to the 15th embodiment in that a wavelength filter 26 is provided between an iris 24 and an image capturing element 15. The rest of the arrangement is the same as the end face observation device 115. In the following explanation, the same reference numerals as in the end face observation device 115 according to the 15th embodiment denote common constituent elements, and a detailed description thereof will be omitted.

More specifically, the wavelength filter 26 provided between the iris 24 and the image capturing element 15 limits the wavelength range of incident light on the image capturing element 15, as in the end face observation device 109 according to the ninth embodiment. It is consequently possible to improve blurs caused by a chromatic aberration generated by an objective lens 12 and a lens 31.

As described above, according to the end face observation device of the 16th embodiment, the quality of an image can further be improved, as in the end face observation device 109 according to the ninth embodiment.

<<17th Embodiment>>

Figure 20:
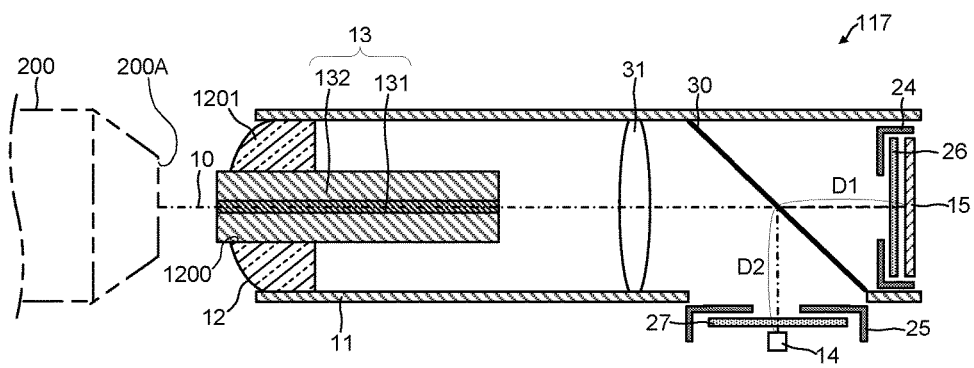
FIG. 20 is a view showing the arrangement of an end face observation device according to the 17th embodiment.

FIG. 20 is a view showing the arrangement of an end face observation device according to the 17th embodiment.

An end face observation device 117 shown in FIG. 20 is different from the end face observation device 116 according to the 16th embodiment in that a wavelength filter 27 is provided between an iris 25 and a light source 14. The rest of the arrangement is the same as the end face observation device 116. In the following explanation, the same reference numerals as in the end face observation device 116 according to the 16th embodiment denote common constituent elements, and a detailed description thereof will be omitted.

More specifically, the wavelength filter 27 provided between the iris 25 and the light source 14 limits the wavelength range of incident light on an image capturing element 15, as in the end face observation device 116 according to the 16th embodiment. It is consequently possible to further improve blurs caused by a chromatic aberration.

As described above, according to the end face observation device of the 17th embodiment, the quality of an image can further be improved, as in the end face observation device 109 according to the ninth embodiment.

<<18th Embodiment>>

Figure 21:
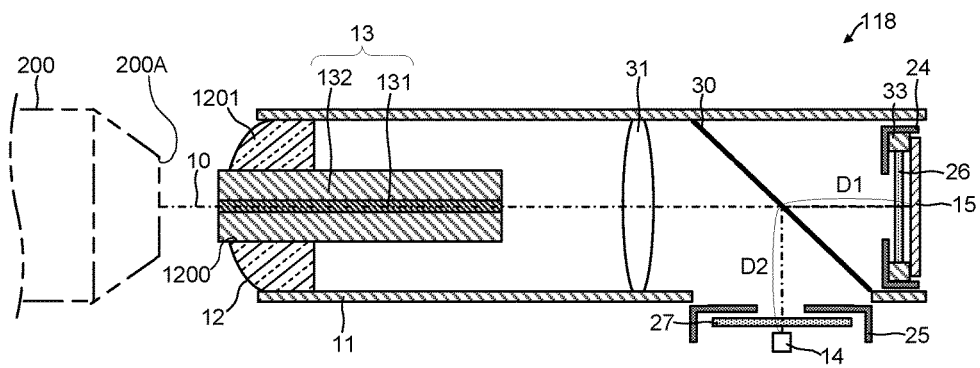
FIG. 21 is a view showing the arrangement of an end face observation device according to the 18th embodiment.

FIG. 21 is a view showing the arrangement of an end face observation device according to the 18th embodiment.

An end face observation device 118 shown in FIG. 21 is different from the end face observation device 117 according to the 17th embodiment in that a light shielding wall 33 is provided near an image capturing element 15. The rest of the arrangement is the same as the end face observation device 117. In the following explanation, the same reference numerals as in the end face observation device 117 according to the 17th embodiment denote common constituent elements, and a detailed description thereof will be omitted.

More specifically, the light shielding wall 33 is arranged between an iris 24 and the image capturing element 15 to surround an optical axis 10. The light shielding wall 33 is a member made of a nontransparent material. This can further suppress incidence of unwanted stray light on the image capturing element 15.

As described above, according to the end face observation device of the 18th embodiment, the light shielding wall 33 is provided in the above-described way, thereby further improving the quality of an image generated by the image capturing element 15.

<<19th Embodiment>>

Figure 22:
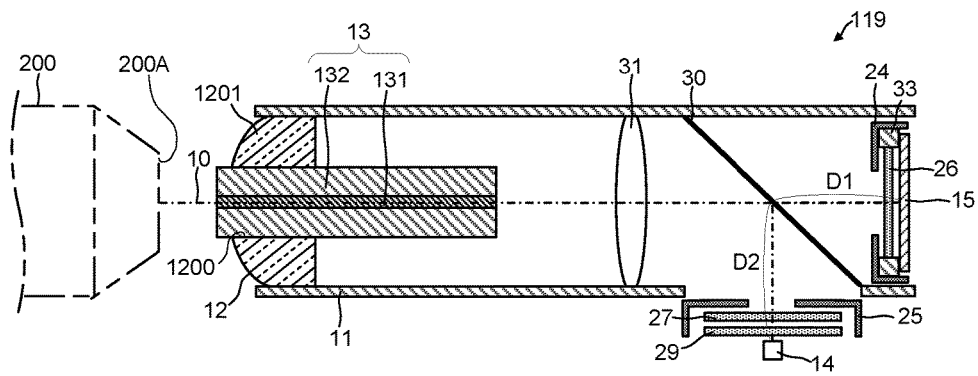
FIG. 22 is a view showing the arrangement of an end face observation device according to the 19th embodiment.

FIG. 22 is a view showing the arrangement of an end face observation device according to the 19th embodiment.

An end face observation device 119 shown in FIG. 22 is different from the end face observation device 118 according to the 18th embodiment in that a polarization filter 29 is provided between a light source 14 and an iris 25. The rest of the arrangement is the same as the end face observation device 118. In the following explanation, the same reference numerals as in the end face observation device 118 according to the 18th embodiment denote common constituent elements, and a detailed description thereof will be omitted.

The reflectance from the transmitting surface of a half mirror 30 changes depending on the polarization direction. For this reason, when the polarization filter 29 is provided between the light source 14 and a wavelength filter 27, only a polarized wave of a low reflectance can be used out of light generated by the light source 14. Hence, stray light can be reduced.

As described above, according to the end face observation device of the 19th embodiment, the quality of an image can further be improved, as in the end face observation device 112 according to the 12th embodiment.

<<20th Embodiment>>

Figure 23:
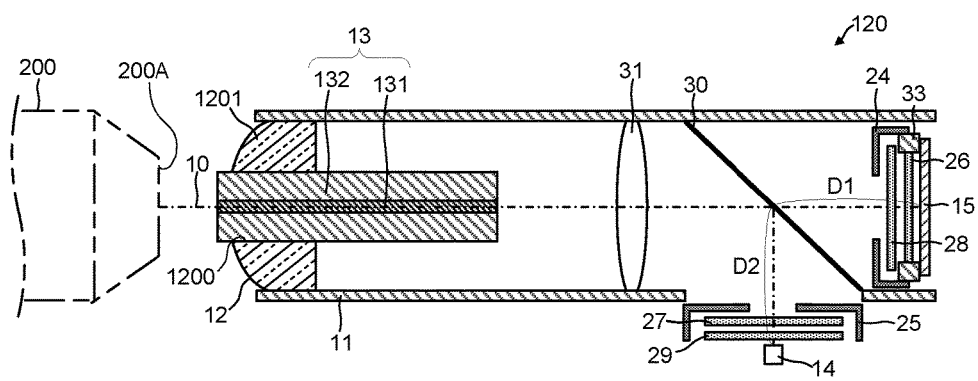
FIG. 23 is a view showing the arrangement of an end face observation device according to the 20th embodiment.

FIG. 23 is a view showing the arrangement of an end face observation device according to the 20th embodiment.

An end face observation device 120 shown in FIG. 23 is different from the end face observation device 119 according to the 19th embodiment in that a polarization filter 28 is provided between an image capturing element 15 and an iris 24. The rest of the arrangement is the same as the end face observation device 119. In the following explanation, the same reference numerals as in the end face observation device 119 according to the 19th embodiment denote common constituent elements, and a detailed description thereof will be omitted.

The polarization filter 28 is provided, for example, near the image capturing element 15 between the iris 24 and a wavelength filter 26. This can make only a polarized wave of a low reflectance enter the image capturing element 15. Hence, stray light can be reduced.

As described above, according to the end face observation device of the 20th embodiment, the quality of an image can further be improved, as in the end face observation device 111 according to the 11th embodiment.

<<21st Embodiment>>

Figure 24:
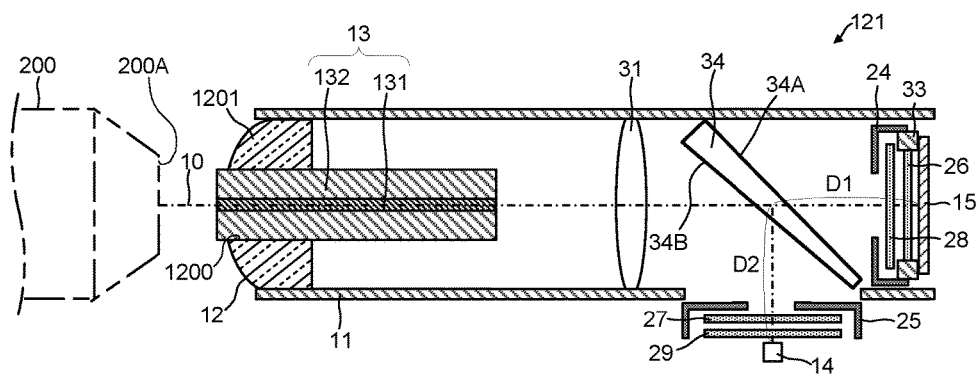
FIG. 24 is a view showing the arrangement of an end face observation device according to the 21st embodiment.

FIG. 24 is a view showing the arrangement of an end face observation device according to the 21st embodiment.

An end face observation device 121 shown in FIG. 24 is different from the end face observation device 120 according to the 20th embodiment in that a half mirror 34 whose reflecting surface and transmitting surface are nonparallel is used in place of the half mirror 30. The rest of the arrangement is the same as the end face observation device 120. In the following explanation, the same reference numerals as in the end face observation device 120 according to the 20th embodiment denote common constituent elements, and a detailed description thereof will be omitted.

The half mirror 34 has a structure in which a reflecting surface 34A that reflects incident light and a transmitting surface 34B that passes the incident light are nonparallel. For example, as shown in FIG. 24, the half mirror 34 has such a shape that decreases the thickness between the reflecting surface 34A and the transmitting surface 34B in one direction. This can reduce the amount of incident light on an image capturing element 15 by shifting the optical path of light reflected by a surface that is not expected to reflect light out of the half mirror 34 and remove unwanted stray light.

As described above, according to the end face observation device of the 21st embodiment, the half mirror 34 whose reflecting surface and transmitting surface are nonparallel is used, thereby further improving the quality of an image generated by the image capturing element 15.

<<22nd Embodiment>>

Figure 25:
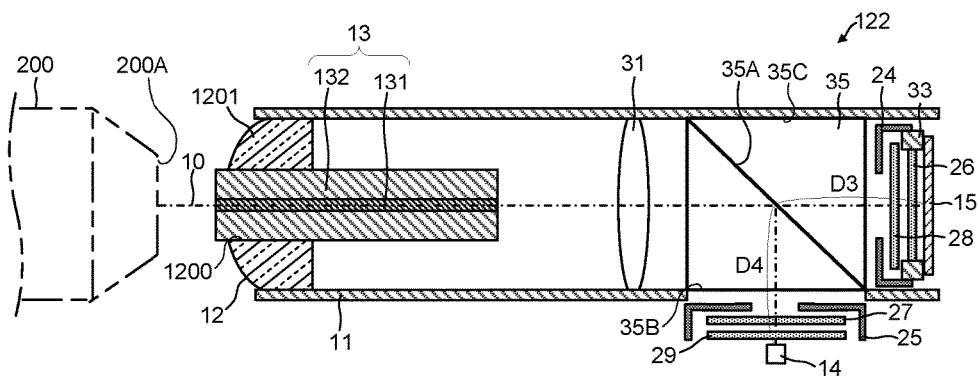
FIG. 25 is a view showing the arrangement of an end face observation device according to the 22nd embodiment.

FIG. 25 is a view showing the arrangement of an end face observation device according to the 22nd embodiment.

An end face observation device 122 shown in FIG. 25 is different from the end face observation device 120 according to the 20th embodiment in that a beam splitter 35 is used in place of the half mirror 30. The rest of the arrangement is the same as the end face observation device 120. In the following explanation, the same reference numerals as in the end face observation device 120 according to the 20th embodiment denote common constituent elements, and a detailed description thereof will be omitted.

The beam splitter 35 is an optical element that partially reflects incident light and partially passes the incident light. The beam splitter 35 divides incident light into reflected light and transmitted light at a predetermined ratio. The beam splitter 35 can be of any type of, for example, a nonpolarization type, an unpolarization type, and a polarization type. According to the beam splitter 35, light from a light source 14 is guided to an optical connector 200, and light from the optical connector 200 is guided to an image capturing element 15.

In this embodiment as well, the light source 14 and the image capturing element 15 are provided at respective positions which are optically conjugate to an objective lens 12 in a confocal optical system via the beam splitter 35. That is, a distance D3 between the image capturing element 15 and a reflecting surface 35A of the beam splitter 35 and a distance D4 between the light source 14 and the reflecting surface 35A of the beam splitter 35 equal.

The beam splitter 35 has a structure in which the relative angle between a transmitting surface 35B facing the light source 14 and the reflecting surface 35A that partially reflects light that enters via the transmitting surface 35B is not 45°, and the relative angle between the reflecting surface 35A and a transmitting surface 35C facing the transmitting surface 35B is not 45°. This can reduce the amount of incident light on the image capturing element 15 by shifting the optical path of light reflected by a surface that is not expected to reflect light out of the beam splitter 35 and remove unwanted stray light.

As described above, according to the end face observation device of the 22nd embodiment, the size can be reduced, as in a case in which a half mirror is used. In addition, since stray light can be removed by applying the beam splitter in which the relative angle between the reflecting surface and the transmitting surface is not 45°, the quality of an image generated by the image capturing element 15 can further be improved.

<<23rd Embodiment>>

Figure 26:
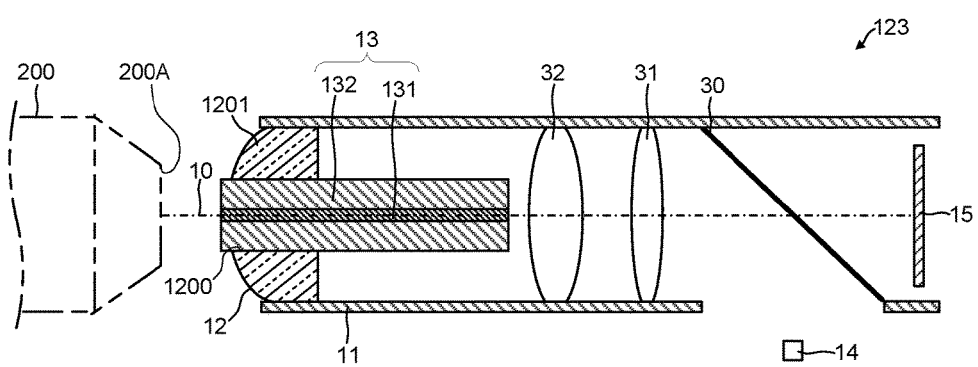
FIG. 26 is a view showing the arrangement of an end face observation device according to the 23rd embodiment.

FIG. 26 is a view showing the arrangement of an end face observation device according to the 23rd embodiment.

An end face observation device 123 shown in FIG. 26 is different from the end face observation device 113 according to the 13th embodiment in that a transparent member 32 is further provided between an objective lens 12 and a lens 31. The rest of the arrangement is the same as the end face observation device 113. In the following explanation, the same reference numerals as in the end face observation device 113 according to the 13th embodiment denote common constituent elements, and a detailed description thereof will be omitted.

As shown in FIG. 26, the end face observation device 123 includes, between the objective lens 12 and the lens 31, the transparent member 32 that propagates both illumination light from a light source 14 and reflected light (image light) from an end face 200A. Here, the transparent member 32 has a shape with a flat surface or curved surface that is not perpendicular to the optical axis. For example, as shown in FIG. 26, the transparent member 32 has a shape with a curved surface as a boundary surface to another medium (for example, air) through which target light propagates. The transparent member 32 can be, for example, a lens having an optical power or a component without an optical power other than a lens.

Note that in the end face observation device 123, the distance between a half mirror 30 and an image capturing element 15 and the distance between the half mirror 30 and the light source 14 can either optically equal or not.

As described above, according to the end face observation device of the 23rd embodiment, when the transparent member 32 is further provided between the objective lens 12 and the lens 31, the optical design freedom further increases, and an obstacle can be avoided more easily, as compared to an optical system including two lenses, that is, the objective lens 12 and the lens 31. This can improve optical performance by, for example, suppressing a chromatic aberration and coma and obtain an image of higher quality. In addition, since the two lenses 31 and 32 are provided between the half mirror 30 and the objective lens 12, the illumination light and the reflected light can share the optical components such as a lens. This can decrease the number of components and attain effects such as easy assembly and cost reduction.

In addition, according to the end face observation device of the 23rd embodiment, since in the transparent member 32, the boundary surface through which target light propagates is not a flat surface perpendicular to the optical axis, the incident power of reflected light from the transparent member 32 to the image capturing element can be reduced as compared to a case in which the boundary surface is a perpendicular flat surface. This can suppress degradation in image quality caused by unwanted light entering the image capturing element 15.

When a lens having an optical power is employed as the transparent member 32, the design freedom of an optical system increases, and an optical system that forms an image of a higher resolution on the image capturing element 15 can easily be designed.

Note that when not a planoconvex or planoconcave lens but a biconvex or concavo-convex lens is used as the lens 31 or 32, stray light caused by reflection on the lens 31 or 32 can be reduced, and therefore, degradation in image quality can further be suppressed. In addition, the stray light caused by reflection can further be reduced by arranging the half mirror 30 at an angle with respect to the optical axis, together with the light source 14 and the like.

<<24th Embodiment>>

Figure 27:
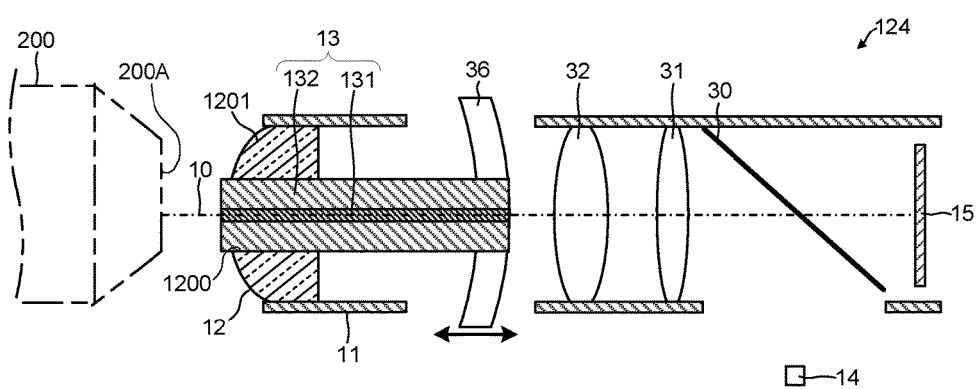
FIG. 27 is a view showing the arrangement of an end face observation device according to the 24th embodiment.

FIG. 27 is a view showing the arrangement of an end face observation device according to the 24th embodiment.

An end face observation device 124 shown in FIG. 27 is different from the end face observation device 123 according to the 23rd embodiment in that a plurality of transparent members are provided between an objective lens 12 and a lens 31. The rest of the arrangement is the same as the end face observation device 123. In the following explanation, the same reference numerals as in the end face observation device 123 according to the 23rd embodiment denote common constituent elements, and a detailed description thereof will be omitted.

As shown in FIG. 27, the end face observation device 124 includes, between the objective lens 12 and the lens 31, transparent members 32 and 36 that propagate both illumination light from a light source 14 and reflected light (image light) from an end face 200A. As in the 23rd embodiment, each of the transparent members 32 and 36 has a shape with a flat surface or curved surface that is not perpendicular to the optical axis. Each of the transparent members 32 and 36 can be a lens having an optical power or a component without an optical power other than a lens. For example, as the component without an optical power, a lens holder made of, for example, a transparent material and configured to hold a lens can be exemplified. Since a general lens holder is formed from an opaque structure, the lens opening is limited by the lens holder, and an image may darken. However, when a lens holder made of a transparent material is used, this problem is solved.

In addition, as shown in FIG. 27, the transparent member 36 may be mechanically connected to a cleaning mechanism 13 and configured to be movable in the optical axis direction. This allows the transparent member 36 to function as the operation portion of the cleaning mechanism 13 and transmit a driving force for pushing in the optical axis direction or feeding of a cleaning tape 131 to the cleaning mechanism 13. When the operation portion of the cleaning mechanism 13 is formed from the transparent member 36, interference between the component and the optical system can be prevented, as compared to a case in which the operation portion is formed from a component of an opaque material. It is therefore possible to suppress unevenness of illumination light or degradation in image quality which occurs when the component blocks illumination light from the light source 14 or reflected light (image light) from the end face 200A.

As described above, according to the end face observation device of the 24th embodiment, a plurality of transparent members are further provided between the objective lens 12 and the lens 31, thereby obtaining an image of higher quality.

In addition, when the transparent member 36 is mechanically connected to the cleaning mechanism 13 and configured to be movable in the optical axis direction, the cleaning mechanism 13 can be operated while suppressing unevenness of illumination light or degradation in image quality. Since this enables an operation (for example, cleaning of the end face 200A of an optical connector 200) on the observation target without moving the end face observation device itself, observation before and after the operation on the observation target is facilitated.

The invention made by the present inventors has been described above in detail based on the embodiments. However, the present invention is not limited to those, and various changes and modifications can be made without departing from the spirit of the invention.

Figure 28A:
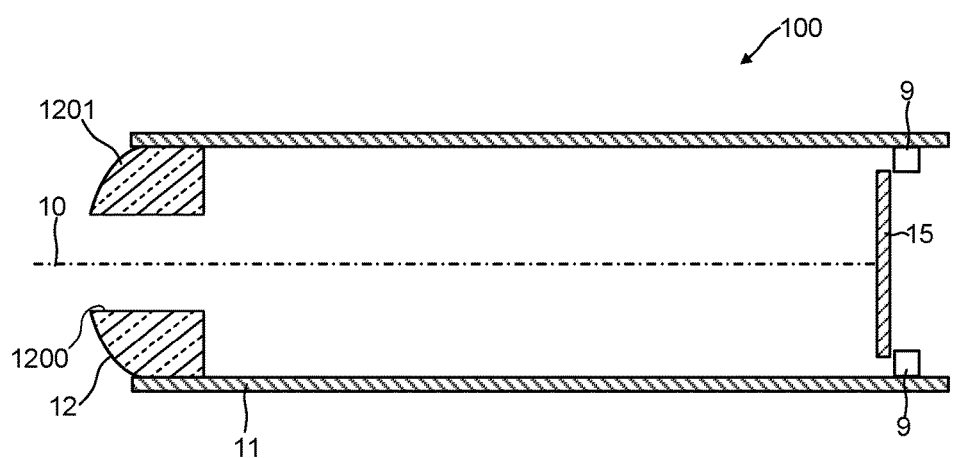
FIG. 28A is a view showing the arrangement of the main body of an end face observation device according to the present invention.
Figure 28B:
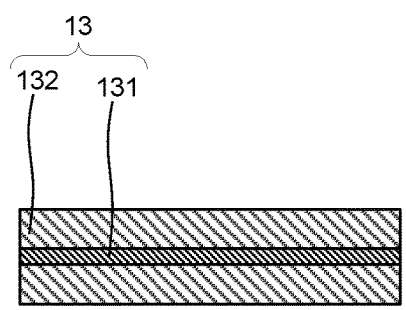
FIG. 28B is a view showing the arrangement of a structure inserted into the end face observation device according to the present invention.

For example, in the above embodiments, an end face observation device in which the main body of the end face observation device and a structure (for example, a cleaning mechanism) are integrated has been exemplified. However, the present invention is not limited to this. For example, the main body of the end face observation device and the structure may be manufactured separately. When the user uses the device, the main body of the end face observation device and the structure may be combined to assemble the end face observation device according to the present invention. For example, as shown in FIGS. 28A and 28B, a main body portion 100 of an end face observation device including the ring-shaped objective lens 12 and the cleaning mechanism 13 may be manufactured separately. When the user uses the device, an end face observation device having a cleaning function may be assembled by inserting the cleaning mechanism 13 into a through hole 1200 of the objective lens 12.

Note that in FIG. 28A, a portion of the end face observation device 101 according to the first embodiment excluding the cleaning mechanism is illustrated as the main body portion 100 of the end face observation device. However, the present invention is not limited to this, and a portion of any one of the end face observation devices 102 to 124 according to the second to 24th embodiments excluding the cleaning mechanism may be used.

In the above embodiments, various examples in which the iris 24, the wavelength filter 26, and the polarization filter 28 are arranged between the image capturing element 15 and the beam splitter 22 (half mirror 30) have been described. However, the present invention is not limited to these examples. For example, at least one of the iris 24, the wavelength filter 26, and the polarization filter 28 may be arranged between the image capturing element 15 and the half mirror 30 or 34 (beam splitter 22 or 35), or the iris 24, the wavelength filter 26, and the polarization filter 28 may be arranged in combination. Similarly, at least one of the iris 25, the wavelength filter 27, and the polarization filter 29 may be arranged between the light source 14 and the half mirror 30 or 34 (beam splitter 22 or 35), or the iris 25, the wavelength filter 27, and the polarization filter 29 may be arranged in combination.

The arrangement of the above-described optical components such as an iris, a wavelength filter, and a polarization filter is not limited to the above-described examples, and the positions of the optical components may be replaced as needed.

In the above embodiments, the cleaning mechanism 13 has been exemplified as a structure provided in the through hole of the objective lens 12 and configured to operate the end face of the optical connector 200. However, the present invention is not limited to this. A prober, a needle sensor device, a processing device, or the like may be arranged and inserted into the through hole 1200 so as to project toward the optical connector 200. Since this enables to observe images before and after an operation of each structure, as in the case of the cleaning mechanism 13, operability can be improved, and the operation time can be shortened.

In the above-described embodiments, a component having a structure that slides the cleaning tape in a predetermined direction has been exemplified as the cleaning mechanism 13. However, the component is not particularly limited as long as it can clean the end face 200A of the optical connector 200.

In the above-described embodiments, an example in which the through hole 1200 serving as the missing portion of the objective lens 12 has a circular shape has been described. However, the shape is not particularly limited as long as it can make a structure such as the cleaning mechanism 13 project toward the optical connector 200. For example, the missing portion of the objective lens 12 may have a U shape.

In the above-described embodiments, to make illumination light from the light source 14 efficiently propagate, the illumination light may be made to propagate not only through the annular portion 1201 of the objective lens 12 but also in the through hole 1200. For example, when part of the cleaner chip 132 inserted into the through hole 1200 is formed from a transparent member, the illumination light can be made to propagate in the through hole 1200.

For the end face observation devices according to the above-described embodiments, a case in which the light source 14 is arranged outside the tubular case 11 has been exemplified. However, the present invention is not limited to this. For example, if the optical path of illumination light need not be blocked, the light source 14 may be arranged in the case 11. In this case, an optical element such as an iris or a wavelength filter arranged on the periphery of the light source 14 is arranged in the case 11, as a matter of course.

For the end face observation devices according to the eighth to 24th embodiments, an arrangement that deflects the illumination light from the light source by an optical element such as a beam splitter or a half mirror has been exemplified. However, the present invention is not limited to this. For example, an arrangement that deflects not the illumination light from the light source but reflected light from the end face (image) of the observation target may be employed. In this case, the image capturing element 15 may be arranged outside the tubular case 11.

In the 24th embodiment, a case in which the transparent member 36 mechanically connected to the structure (cleaning mechanism 13) is provided in the end face observation device according to the 23rd embodiment has been exemplified. However, the present invention is not limited to this. For example, the transparent member 36 may be provided in one of the end face observation devices according to the first to 22nd embodiments.

In addition, an arrangement in which the transparent member has a shape with a flat surface or curved surface that is not perpendicular to the optical axis has been exemplified. However, even another optical element such as the objective lens 12 or the lens 16 can obviously have the same effect.

INDUSTRIAL APPLICABILITY

The end face observation device according to the present invention can widely be used for, for example, cleaning or observation of various kinds of components represented by an optical connector used to connect various kinds of network devices and optical fibers.

EXPLANATION OF THE REFERENCE NUMERALS AND SIGNS

100 . . . main body of end face observation device, 101-105, 106A-106E, 107-124 . . . end face observation device, 200 . . . optical connector, 200A . . . end face of optical connector, 10 . . . optical axis, 11 . . . case, 12 . . . objective lens, 1200 . . . through hole, 1201 . . . annular portion, 13, 20 . . . cleaning mechanism, 131 . . . cleaning tape, 132 . . . cleaner chip, 133 . . . light valve, 9, 9_1, 9_2, 14 . . . light source, 15 . . . image capturing element, 16 . . . lens, 17 . . . transparent member, 18 . . . deflecting mirror, 19, 21 . . . light shielding plate, 22, 35 . . . beam splitter, 23 . . . lens, 24, 25 . . . iris, 26, 27 . . . wavelength filter, 28, 29 . . . polarization filter, 30, 34 . . . half mirror, 31 . . . lens, 32 . . . transparent member, 33 . . . light shielding wall, 23, 24 . . . polarization filter, 36 . . . transparent member, D1-D4 . . . distance

The invention claimed is:

1. An end face observation device comprising:
a first lens including a missing portion extending through in an optical axis direction; a light source configured to generate light that irradiates an end face of an observation target via said first lens;
an image capturing element configured to receive an image of the end face of the observation target via said first lens; and
a structure inserted into the missing portion of said first lens and configured to operate upon the end face of the observation target.

2. An end face observation device according to claim 1, wherein said structure includes a cleaning mechanism configured to clean the end face of the observation target.

3. An end face observation device according to claim 1, wherein said light source and said first lens are arranged coaxially.

4. An end face observation device according to claim 1, wherein said first lens has a ring shape.

5. An end face observation device according to claim 3, wherein said light source has a ring shape.

6. An end face observation device according to claim 3, further comprising a tubular case,
wherein said first lens and said structure are arranged at one end of said tubular case,
said light source and said image capturing element are arranged at the other end of said tubular case, and
illumination light from said light source and reflected light from the end face of the observation target propagate through a common space in said case.

7. An end face observation device according to any one of claims 1, 2 to 6, further comprising a second lens provided on an optical axis between said first lens and said image capturing element.

8. An end face observation device according to claim 7, further comprising a transparent member provided on the optical axis between said first lens and said second lens.

9. An end face observation device according to claim 1, further comprising an optical element provided on an optical axis between said first lens and said image capturing element and configured to partially reflect incident light and partially passes the incident light.

10. An end face observation device according to claim 9, wherein said optical element comprises one of a beam splitter and a half mirror.

11. An end face observation device according to claim 9, wherein said optical element comprises a half mirror whose reflecting surface and transmitting surface are nonparallel.

12. An end face observation device according to claim 9, wherein said optical element comprises a beam splitter, said beam splitter having a transmitting surface facing said light source and a reflecting surface that partially reflects light that enters via the transmitting surface, wherein a relative angle between the transmitting surface and the reflecting surface is not 45°.

13. An end face observation device according to claim 9, further comprising a second lens provided on an optical axis between said optical element and said image capturing element.

14. An end face observation device according to claim 9, further comprising a second lens provided on an optical axis between said first lens and said optical element.

15. An end face observation device according to claim 14, further comprising a third lens provided on the optical axis between said first lens and said second lens.

16. An end face observation device according to claim 9, further comprising a condensing lens provided on an optical axis between said light source and said optical element.

17. An end face observation device according to claim 9, further comprising at least one of an iris, a wavelength filter, and a polarization filter on an optical axis between said image capturing element and said optical element.

18. An end face observation device according to claim 9, further comprising at least one of an iris, a wavelength filter, and a polarization filter on an optical axis between said light source and said optical element.

19. An end face observation device according to any one of claims 9 to 18 further comprising a transparent material provided on the optical axis between said first lens and said optical element.

20. An end face observation device according to any one of claims 9 to 18, further comprising an operation portion provided on the optical axis between said first lens and said optical element and made of a transparent material, wherein said operation portion is connected to said structure and is movable in the optical axis direction.

21. An end face observation device according to any one of claims 9 to 18, wherein said light source and said image capturing element are arranged at respective positions of different optical distances from said optical element.

22. An end face observation device according to any one of claims 9 to 18, wherein said light source and said image capturing element are arranged at respective positions of an equal optical distance from said optical element.

23. An end face observation device according to any one of claims 9 to 18, wherein said light source and said image capturing element are arranged at respective positions which are optically conjugate to said first lens.

24. An end face observation device according to any one of claim 1 or 2, wherein said structure further includes an optical member formed from a transparent member other than air and configured to guide illumination light from said light source to the end face of the observation target.

* * * * *